US 7,005,287 B1

(12) United States Patent
Christensen et al.

(10) Patent No.: US 7,005,287 B1
(45) Date of Patent: Feb. 28, 2006

(54) PROCESS FOR THE ENZYMATIC MODIFICATION OF PECTIN

(75) Inventors: Tove Martel Ida Else Christensen, Allerod (DK); Jette Dina Kreiberg, Roskilde (DK)

(73) Assignee: Danisco A/S, Copenhagen K (DK)

( * ) Notice: Subject to any disclaimer, the term of this patent is extended or adjusted under 35 U.S.C. 154(b) by 195 days.

(21) Appl. No.: 10/018,604

(22) PCT Filed: Jun. 15, 2000

(86) PCT No.: PCT/IB00/00869

§ 371 (c)(1),
(2), (4) Date: Jun. 25, 2002

(87) PCT Pub. No.: WO00/78982

PCT Pub. Date: Dec. 28, 2000

(30) Foreign Application Priority Data

Jun. 17, 1999 (GB) .................................. 9914209

(51) Int. Cl.
C12N 9/16 (2006.01)
C12N 9/18 (2006.01)
C12N 9/24 (2006.01)
C12N 1/20 (2006.01)
C07H 21/04 (2006.01)

(52) U.S. Cl. ...................... 435/196; 435/197; 435/200; 435/252.3; 435/320.1; 536/23.2

(58) Field of Classification Search ................ 435/196, 435/183, 197, 200, 252.3, 320.1; 536/23.2, 536/23.1
See application file for complete search history.

(56) References Cited

U.S. PATENT DOCUMENTS

| 5,296,376 A | 3/1994 | Bridges ..................... 435/320.1 |
| 5,413,937 A | 5/1995 | Bridges ..................... 435/320.1 |
| 5,449,764 A | 9/1995 | Bird ............................ 536/23.2 |
| 5,484,906 A | 1/1996 | Bird ............................... 800/298 |
| 5,945,580 A | 8/1999 | Dunsmuir ..................... 800/298 |
| 6,083,540 A | 7/2000 | Christensen .................. 426/50 |
| 6,268,195 B1 | 7/2001 | Christensen ................ 435/196 |
| 6,271,033 B1 | 8/2001 | Bridges ....................... 435/468 |
| 6,372,477 B1 | 4/2002 | J.theta.rsboe ............... 435/233 |
| 2003/0157230 A1 | 8/2003 | Christensen ................ 426/564 |

FOREIGN PATENT DOCUMENTS

| EP | 0 271 988 A2 | 6/1988 |
| EP | 0 532 060 A1 * | 3/1993 |
| EP | 0 577 252 A1 | 1/1994 |
| WO | WO 97/03574 | 2/1997 |
| WO | WO 97 10328 | 3/1997 |
| WO | WO 97/31102 | 8/1997 |
| WO | WO 97/38591 | 10/1997 |
| WO | WO 2000 078982 | 12/2000 |
| WO | WO 2002 016613 | 2/2002 |

(Continued)

OTHER PUBLICATIONS

Alignment between Applicants SEQ ID NO: 1 and Accession No. A15981 [100% identical(DNA)].*

(Continued)

Primary Examiner—Tekchand Saidha
(74) Attorney, Agent, or Firm—Nixon & Vanderhye P.C.

(57) ABSTRACT

A process for modifying a pectin comprising providing a host having PME activity and PG activity; transforming said host by silencing PG activity thereby to provide an increased PME to PG ratio; preparing a PME extract from the transformed host; using the PME extract to modify pectin.

20 Claims, 1 Drawing Sheet

FOREIGN PATENT DOCUMENTS

| WO | WO 2002 063018 | 8/2002 |
|---|---|---|
| WO | WO 2003 098186 | 11/2003 |

OTHER PUBLICATIONS

Alignment between Applicants' SEQ ID NO: 2 and Accession No. AAR 32107 [100% identical (protein)].*

Grierson et al. Nucleic Acids Research, vol. 14, pp. 8595-8603.*

Sequence alignment between Accession No. A24194 & Applicants' SEQ ID NO: 1 (DNA) are 100% identical [EP 0 532 060 A1].*

Sequence alignment between Accession No. AAR32107 & Applicants' SEQ ID NO: 2 (enzyme, polygalacturonase) are 100% identical [EP 0 532 060 A1].*

Daas, P.J.H., et al., "*Investigation of the non-esterified galacturonic acid distribution in pectin with endopolygalacturonase,*" Carbohydrate Research, NL, Elsevier Scientific Publishing Company, Amsterdam, vol. 318, No. 1-4, May 31, 1999, pp. 135-145.

International Search Report for PCT/US00/00869 (3 pages).

Lacoux, J., Protoplasma (2003), 222 (3-4), 205-209 (abstract).

Moffatt, et al, Plant Physiology (2002), 128(3), 812-821 (abstract).

Smith CJS, et al, J. Cell. Biochem (1991) Suppl. 15D, 27 (abstract).

NCBI Accession No. A24194, Mar. 17, 1993.
NCBI Accession No. AR364905.1, Sep. 5, 1995.
NCBI Accession No. A15981.1, Jun. 22, 1988.
NCBI Accession No. AX062336.1, Dec. 28, 2000.
NCBI Accession No. X04583.1 (1986).
NCBI Accession No. X05656.1 (1987).
NCBI Accession No. I01809.1 (1989).
NCBI Accession No. AJ505750.1 (2002).
NCBI Accession No. LES505947.1 (2002).
NCBI Accession No. AF152758.1 (2000).
NCBI Accession No. AY043233.1 (2001).
NCBI Accession No. M37304.1 (1988).
NCBI Accession No. X14074.1 (1988).
NCBI Accession No. AK117942 (2002).
NCBI Accession No. AX412563.1 (2002).

* cited by examiner

FIG. 1.

DNA sequence of pTom 6

PROCESS FOR THE ENZYMATIC MODIFICATION OF PECTIN

CROSS REFERENCE TO RELATED APPLICATIONS

This application is the U.S. National Phase under 35 U.S.C. § 371 of International Application No. PCT/IB00/00869, filed on Jun. 15, 2000, which was published in English and claims priority to Great Britain patent application number 9914209.3, filed Jun. 17, 1999. This Great Britain patent application is herein incorporated by reference.

FIELD OF THE INVENTION

The present invention relates to a process.

In particular, the present invention relates to a process which comprises the use of an enzyme.

More in particular, the present invention relates to a process for enzymatically modifying pectin.

BACKGROUND OF THE INVENTION

Pectin is a structural polysaccharide commonly found in the form of protopectin in plant cell walls. The backbone of pectin comprises α-1-4 linked galacturonic acid residues which are interrupted with a small number of 1,2 linked α-L-rhamnose units.

In addition, pectin comprises highly branched regions with an almost alternating rhamno-galacturonan chain. These highly branched regions also contain other sugar units (such as D-galactose. L-arabinose and xylose) attached by glycosidic linkages to the C3 or C4 atoms of the rhamnose units or the C2 or C3 atoms of the galacturonic acid units. The long chains of α-1-4 linked galacturonic acid residues are commonly referred to as "smooth" regions, whereas the highly branched regions are commonly referred to as the "hairy regions".

Some of the carboxyl groups of the galacturonic residues are esterified (e.g. the carboxyl groups are methylated). Typically esterification of the carboxyl groups occurs after polymerisation of the galacturonic acid residues. However, it is extremely rare for all of the carboxyl groups to be esterified (e.g. methylated).

Usually, the degree of esterification will vary from 0–90%. If 50% or more of the carboxyl groups are esterified then the resultant pectin is referred to as a "high ester pectin" ("HE pectin" for short) or a "high methoxyl pectin". If less than 50% of the carboxyl groups are esterified then the resultant pectin is referred to as a "low ester pectin" ("LE pectin" for short) or a "low methoxyl pectin". If 50% of the carboxyl groups are esterified then the resultant pectin is referred to as a "medium ester pectin" ("ME pectin" for short) or a "medium methoxyl pectin". If the pectin does not contain any—or only a few—esterified groups it is usually referred to as pectic acid.

The structure of the pectin, in particular the degree of esterification (e.g. methylation), dictates many of the resultant physical and/or chemical properties of the pectin. For example, pectin gelation depends on the chemical nature of the pectin, especially the degree of esterification. In addition, however, pectin gelation also depends on the soluble-solids content, the pH and calcium ion concentration. With respect to the latter, it is believed that the calcium ions form complexes with free carboxyl groups, particularly those on a LE pectin.

Pectic enzymes such as pectin methylesterases (EC 3.1.1.11), are classified according to their mode of attack on the galacturonan part of the pectin molecule. In more detail. PME activity produces free carboxyl groups and free methanol. The increase in free carboxyl groups can be easily monitored by automatic titration. In this regard, earlier studies have shown that some PMEs de-esterify pectins in a random manner, in the sense that they de-esterify any of the esterified (e.g. methylated) galacturonic acid residues on one or more than one of the pectin chains. Examples of PMEs that randomly de-esterify pectins may be obtained from fungal sources such as *Aspergillus aculeatus* (see WO 94/25575) and *Aspergillus japonicus* (Ishii et al 1980 J Food Sci 44 pp 611–14). Baron et al (1980 Lebensm. Wiss. M-Technol 13 pp 330–333) apparently have isolated a fungal PME from *Aspergillus niger*. This fungal PME is reported to have a molecular weight of 39000 D, an isoelectric point of 3.9, an optimum pH of 4.5 and a $K_m$ value (mg/ml) of 3.

In contrast, some PMEs are known to de-esterify pectins in a block-wise manner, in the sense that it is believed they attack pectins either at non-reducing ends or next to free carboxyl groups and then proceed along the pectin molecules by a single-chain mechanism, thereby creating blocks of un-esterified galacturonic acid units which can be calcium sensitive. Examples of such enzymes that block-wise enzymatically de-esterify pectin are plant PMEs. Up to 12 isoforms of PME have been suggested to exist in citrus (Pilnik W. and Voragen A. G. J. (Food Enzymology (Ed.: P. F. Fox); Elsevier; (1991); pp: 303–337). These isoforms have different properties.

Random or blockwise distribution of free carboxyl groups can be distinguished by high performance ion exchange chromatography (Schols et al Food Hydrocolloids 1989 6 pp 1115–121). These tests are often used to check for undesirable, residual PME activity in citrus juices after pasteurisation because residual PME can cause, what is called, "cloud loss" in orange juice in addition to a build up of methanol in the juice.

PME substrates, such as pectins obtained from natural plant sources, are generally in the form of a high ester pectin having a DE of about 70%. Sugar must be added to extracts containing these high ester PME substrates to provide sufficient soluble solids to induce gelling. Usually a minimum of 55% soluble solids is required. Syneresis tends to occur more frequently when the percentage soluble solids is less than 55%. When syneresis does occur, expensive additives must be used to induce gelling.

Versteeg et al (J Food Sci 45 (1980) pp 969–971) apparently have isolated a PME from orange. This plant PME is reported to occur in multiple isoforms of differing properties. Isoform I has a molecular weight of 36000 D, an isoelectric point of 10.0, an optimum pH of 7.6 and a $K_m$ value (mg/ml) of 0.083. Isoform II has a molecular weight of 36200 D, an isoelectric point of 11.0, an optimum pH of 8.8 and a $K_m$ value (mg/ml) of 0.0046. Isoform III (HMW-PE) has a molecular weight of 54000 D, an isoelectric point of 10.2, an optimum pH of 8 and a $K_m$ value (mg/ml) of 0.041. However, to date there has been very limited sequence data for such PMEs.

According to Pilnik and Voragen (ibid), PMEs may be found in a number of other higher plants, such as apple, apricot, avocado, banana, berries, lime, grapefruit, mandarin, cherries, currants, grapes, mango, papaya, passion fruit, peach, pear, plums, beans, carrots, cauliflower, cucumber, leek, onions, pea, potato, radish and tomato. However, likewise, to date there has been very limited sequence data for such PMEs.

A plant PME has been reported in WO-A-97/03574 (the contents of which are incorporated herein by reference). This PME has the following characteristics: a molecular weight of from about 36 kD to about 64 kD; a pH optimum of pH 7–8 when measured with 0.5% lime pectin in 0.15 M NaCl; a temperature optimum of at least 50° C.; a temperature stability in the range of from 10°—at least 40° C.; a $K_m$ value of 0.07%; an activity maximum at levels of about 0.25 M NaCl; an activity maximum at levels of about 0.2 M $Na_2SO_4$; and an activity maximum at levels of about 0.3 M $NaNO_3$.

Another PME has been reported in WO 97/31102 (the contents of which are incorporated herein by reference).

PMEs have important uses in industry. For example, they can be used in or as sequestering agents for calcium ions. In this regard, and according to Pilnik and Voragen (ibid), cattle feed can be prepared by adding a slurry of calcium hydroxide to citrus peels after juice extraction. After the addition, the high pH and the calcium ions activate any native PME in the peel causing rapid de-esterification of the pectin and calcium pectate coagulation occurs. Bound liquid phase is released and is easily pressed out so that only a fraction of the original water content needs to be removed by expensive thermal drying. The press liquor is then used as animal feed.

As indicated above, a PME has been obtained from *Aspergillus aculeatus* (WO 94/25575). Apparently, this PME can be used to improve the firmness of a pectin-containing material, or to de-methylate pectin, or to increase the viscosity of a pectin-containing material.

It has also become common to use PME in the preparation of foodstuffs prepared from fruit or vegetable materials containing pectin—such as jams or preservatives. For example. WO-A-94/25575 further reports on the preparation of orange marmalade and tomato paste using PME obtained from *Aspergillus aculeatus*.

JP-A-63/209553 discloses gels which are obtained by the action of PME, in the presence of a polyvalent metal ion, on a pectic polysaccharide containing as the main component a high-methoxyl poly α-1,4-D-galacturonide chain and a process for their production.

Pilnik and Voragen (ibid) list uses of endogenous PMEs which include their addition to fruit juices to reduce the viscosity of the juice if it contains too much pectin derived from the fruit, their addition as pectinase solutions to the gas bubbles in the albedo of citrus fruit that has been heated to a core temperature of 20° C. to 40° C. in order to facilitate removal of peel and other membrane from intact juice segments (U.S. Pat. No. 4,284,651), and their use in protecting and improving the texture and firmness of several processed fruits and vegetables such as apple (Wiley & Lee 1970 Food Technol 24 1168–70), canned tomatoes (Hsu et al 1965 J Food Sci 30 pp 583–588) and potatoes (Bartolome & Hoff 1972 J Agric Food Chem 20 pp 262–266).

Glahn and Rolin (1994 Food Ingredients Europe, Conf Proceedings pp 252–256) report on the hypothetical application of the industrial "GENU pectin type YM-100" for interacting with sour milk beverages. No details are presented at all on how GENU pectin type YM-100 is prepared.

EP-A-0664300 discloses a chemical fractionation method for preparing calcium sensitive pectin. This calcium sensitive pectin is said to be advantageous for the food industry.

The fruit ripening process has been extensively used as a model system to dissect genetically programmed organ differentiation. Studies with both non climacteric and climacteric fruits such as apples, bananas, tomatoes, pears, avocados and mangos, have provided evidence for differential gene expression during ripening. In particular, pectin degrading enzymes such as PME and polygalacturonase (PG) have been implicated in the biochemical conversion of pectic cell wall substances during fruit ripening. By way of example, enzymes, such as PME and PG, showing altered activities during ripening have been reported and the respective genes have been cloned (D. Grierson, 1985, CRC Critical Reviews in Plant Sciences 3, 113–132). The features of many of these genes have not been defined. However, one such gene has been shown to produce PG, the enzyme primarily responsible for degrading the cell wall. The synthesis of PG begins in tomatoes during early stages of ripening, and reaches a maximum at the soft red stage. This increase is paralleled closely by an increase in PG mRNA (Grierson et al. 1985, Plant 163, pp. 263–271). According to one hypothesis, PG solubilises pectic fragments during early ripening stages, and reduces the molecular weight of pectin fragments during later stages of ripening.

SUMMARY OF THE INVENTION

An important factor in loss of pectin integrity (decrease in the polymer size and subsequent loss of viscosity) during commercial processing of tomatoes is enzymatic degradation of pectin by PG which substantially reduces the length of the pectin backbone. PMEs, de-esterify HE pectins to LE pectins or pectic acids. Pectins demethylated by PME are believed to be the substrate for PG which has the potential to act in an uncontrolled fashion in fruit tissues and can rapidly degrade pectin polymers resulting in a substantially shortened pectin backbone.

The present invention seeks to overcome the problems associated with the prior art processes.

The present invention thus provides a process for modifying a pectin by silencing PG activity in a transformed host so that an alteration in the ratio of PME to pectin degrading enzymes is obtained.

The present invention also provides a process for modifying a pectin by creating a transformed host comprising a silenced PG activity so that an elevated ratio of PME to PG is obtained.

According to a first aspect of the present invention there is provided a process for modifying a pectin comprising (i) providing a host having PME activity and PG activity;
(ii) transforming said host by silencing PG activity thereby to provide an increased PME to PG ratio;
(iii) preparing a PME extract from the transformed host;
(iv) using the PME extract to modify pectin.

According to a second aspect of the present invention there is provided a PME modified pectin prepared by the process according to the present invention.

According to a third aspect of the present invention there is provided a foodstuff comprising a PME modified pectin prepared by the process according to the present invention.

According to a fourth aspect of the present invention there is provided use of a PME as herein defined to reduce the number of ester groups in a pectin and preferably in a block-wise manner.

According to a fifth aspect of the present invention there is provided the use of a PME as herein defined to de-esterify two or more adjacent galacturonic acid residues of a pectin.

DETAILED DESCRIPTION OF THE INVENTION

The present invention is based on the highly surprising finding that it is possible to silence PG activity by differentially regulating the relative level of expression of PME and PG so that
(i) an elevated ratio of PME to PG is obtained
(ii) a PME is obtained which is relatively free of PG and which is capable of modifying pectin by, for example, degrading via blockwise de-esterification crude or pure extracts of homogenised fruit tissues comprising pectin polymers in a controlled fashion.
(iii) a modified pectin of relatively high molecular weight (50 kDa to 200 kDa) is obtained.

A further advantage is that in some embodiments the PME of the present invention may be capable of producing a substantially homogeneous block-wise de-esterified pectin. By this we mean that substantially all of the pectin chains comprise at least two adjacent de-esterified carboxyl groups. However, for some applications it may not be necessary to prepare or use such a substantially homogeneous block-wise de-esterified pectin.

In accordance with the present invention, the modified pectin such as the de-esterified pectin of the present invention is advantageous for the preparation of a foodstuff.

The use of a block-wise enzymatically de-esterified pectin—which is preferably prepared by the process of the present invention—is advantageous as it allows proteins such as whey and milk proteins (such as casein) to be stable in acidic solutions. This is of importance for the drinks market, such as drinking yoghurt, acidified milk beverage, fruit juice/milk beverage and whey or soya protein drinks, wherein before it was only possible to retain the stability of the key protein system under fairly high acidic conditions—such as pH 4.2—if high amounts of stabiliser were present.

We have now found that for some applications even small amounts of the de-esterified pectin prepared by the process of the present invention may be employed. At these low levels, the de-esterified pectin according to the present invention not only acts as a stabiliser but it is of benefit as even small amounts of de-esterified pectin can act as a stabiliser and can perform better than other pectins.

If desired, the use of the de-esterified pectin of the present invention would enable food manufacturers to increase the pH of foods, such as drinks. In this regard, in some cases the less acidic nature of the drinks may make them more palatable for people, especially infants. Thus, in contrast to the prior art processes, it is now possible to retain the flavour of those proteins at pH conditions higher than 4.2, such as up to pH 5.5 (such as pH 5.2) by use of the block-wise enzymatically de-esterified pectin, particularly the block-wise enzymatically de-esterified pectin prepared by use of the process of the present invention.

In addition, it is believed that even under low pH conditions, such as pH 4.2 or less, the block-wise enzymatically de-esterified pectin—particularly the block-wise enzymatically de-esterified pectin (preferably prepared by use of the present invention)—stabilises the protein(s) more than the prior art stabilisers that are used for those pH conditions.

Without wishing to be bound by theory it is believed that the block-wise enzymatically de-esterified pectin—particularly that prepared by use of the techniques of the present invention—stabilises the protein(s) by surrounding the protein(s) in a blanket of negative charges, thus forming a stable suspension.

The process for esterifying pectins is advantageous because it obviates the need for the high temperature and methanol esterification conditions associated with the prior art processes. The PME enzyme may de-esterify the PME substrates in a random manner or in a block-wise manner (see WO 98/47391). In addition, in some instances, de-esterifying pectins can increase the calcium ion sensitivity of a pectin—which in turn may be advantageous.

Other aspects and advantages of the present invention are presented in the accompanying claims and the following discussion.

The term "pectin" includes pectin in its normal sense, as well as fractionates and derivatives thereof, as well as modified pectins such as pectin derivatives, chemically modified pectins and enzymatically modified pectins. An example of a pectin derivative is pectin that has been chemically treated—eg. amidated. The term also includes pectins that have been prior treated with an enzyme such as a PME—which may be derived from the same source as the PME of the present invention or a different PME or a combination thereof.

The modified pectin of the present invention is a pectin that has been treated with a crude or pure extract comprising an elevated ratio of PME enzyme to PG enzyme or a purified fraction thereof which has been prepared by the process of the present invention.

The process for modifying a pectin using the PME enzyme of the present invention is useful for blockwise de-esterifying pectins when the pectins are contacted with the enzyme in a substantially aqueous medium.

Alternatively, the process for modifying a pectin using the PME enzyme of the present invention is useful for esterifying pectins when the pectins are contacted with the enzyme in a substantially non-aqueous medium, such as in the presence of methanol or in the presence of high concentrations of ammonium sulphate.

Preferably, the PME modified pectin is a high ester pectin.
Preferably, the PME modified pectin of the present invention contains from about 55% to about 85% ester groups.
Preferably, the PME modified pectin of the present invention contains from about 70% to about 80% ester groups.
Preferably, the PME modified pectin of the present invention contains from about 72% to about 80% ester groups.
Preferably, the PME modified pectin of the present invention contains from about 74% to about 80% ester groups.
Preferably, the PME modified pectin of the present invention contains from about 76% to about 80% ester groups.
Preferably, the PME modified pectin has a molecular weight from about 50 kDa to about 200 kDa.
Preferably, the PME modified pectin has a molecular weight of about 100 kDa.
Preferably the PME modified pectin is prepared in the presence of sodium ions.
Preferably, the sodium ions are derived from NaCl, $NaNO_3$ or $Na_2SO_4$ or combinations thereof.
Preferably, the process includes the further step of isolating the PME modified pectin from the active PME.
Preferably, the process includes the further step of adding the PME modified pectin of the present invention to a medium that is suitable for consumption.
Preferably, the medium is an acidic environment.
Preferably, the acidic environment has a pH of from about 3.5 to about 5.5, preferably wherein the acidic environment has a pH of from 4 to about 5.5.
Preferably, the acidic environment has a pH of about 4.
Preferably, the medium is an aqueous solution.
Preferably, the aqueous solution is a beverage.

Preferably, the beverage is an acidified milk beverage, a drinking yoghurt, a fruit juice/milk beverage or an acidified beverage comprising whey protein or protein of vegetable origin such as soya.

Preferably, the medium comprises a protein.

Preferably, the protein is derived from or is derivable from or is in a dairy product, such as milk or cheese.

Preferably, the protein is casein or whey protein.

Preferably, the foodstuff is food for human and/or animal consumption. Typical preferred foodstuffs include jams, marmalades, jellies, dairy products (such as milk or cheese), meat products, poultry products, fish products and bakery products. The foodstuff may even be a beverage. The beverage can be a drinking yoghurt a fruit juice or a beverage comprising whey protein.

In addition to the foodstuff comprising the PME modified pectin produced by the process of the present invention, the foodstuff may comprise more other components, such as one or more suitable food ingredients. Typical food ingredients include any one or more of an acid—such as citric acid—or a sugar—such as sucrose, glucose or invert sugar—or fruit—or other enzymes, preservatives, colourings and other suitable components.

In one preferred embodiment, the foodstuff comprising the PME modified pectin produced by the process of the present invention, comprises fruit. Here, fruit imparts taste, colour and structure to the foodstuff, as well as pectin, acid and a small amount of solids. Depending on the level of natural flavour and colour in the fruit, fruit dosages are normally from 25% to 60% of the jam. The solids content of ordinary fruit is around 10% Brix, but fruit concentrate, which is typically 65–70% Brix, can also be used. The pH in fruit varies widely, depending on the fruit in question, but most fruits have a pH between 3.0 and 3.5.

The term "silenced" or "silencing" in the context of the present invention includes any method or entity capable of eventually modulating PG activity such as but not limited to inhibiting, suppressing or downregulating the expression of the nucleotide sequence encoding the native PG enzyme or a PG associated nucleotide sequence or by inhibiting native PG activity or by encoding a product that inhibits the expression or activity of the native PG enzyme. An example of such an entity may include but is not limited to an antibody which is immunologically reactive with the native PG enzyme as defined herein.

In one embodiment, the present invention relates to a nucleotide sequence capable of silencing native PG activity such as by silencing native PG expression or activity or by encoding a product that inhibits native PG expression or activity.

The term "nucleotide" in relation to the present invention includes genomic DNA, cDNA, synthetic DNA, and RNA. Preferably it means DNA, more preferably cDNA for the coding sequence of the present invention.

The present invention also relates to a construct expressing or comprising a nucleotide sequence of the present invention.

The term "construct"—which is synonymous with terms such as "conjugate", "cassette" and "hybrid" comprises (i) the nucleotide sequence of the present invention (ii) a promoter capable of expressing a nucleotide sequence in an organism and (iii) a 3' termination sequence.

The present invention also relates to a vector (including a plasmid) expressing or comprising a construct of the present invention.

The present invention also relates to a combination of constructs comprising at least the construct of the present invention and a second construct comprising a nucleotide sequence of interest (NOI) and a promoter.

The present invention also relates to a transformed host comprising the nucleotide sequence according to the present invention or a construct according to the present invention or a vector according to the present invention or a combination of constructs according to the present invention.

The term "host" includes but is not limited to an organism, organ, tissue or cell.

The term "transformed host" in relation to the present invention includes any organism as herein defined but wherein some or all of the native PG activity is silenced by expression of a nucleotide sequence according to the present invention or a construct according to the present invention or a vector according to the present invention or a combination of constructs according to the present invention.

The term "organism" in relation to the present invention includes any organism expressing or comprising a cell, tissue or organ expressing or comprising a nucleotide sequence encoding a native PG enzyme and/or products obtainable therefrom and wherein a native promoter allows expression of the native PG nucleotide sequence in its natural environment when present in the organism. In the context of the present invention, the term "native" is used interchangeably with the term "natural" "naturally occurring", "genomic" and "endogenous".

As used with reference to the present invention, the terms "expression", "expresses", "expressed" and "expressable" are synonymous with the respective terms "transcription", "transcribes", "transcribed" and "tanscribable". Hence, if the nucleotide sequence is a coding sequence, then the product of its expression may also be called the transcription product and visa versa. Likewise, if the nucleotide sequence is an anti-sense nucleotide sequence then the product of its transcription may also be called the expression product and vice versa.

In one embodiment, preferably the host is a plant.

The term "plant" includes but is not limited to angiosperms, gymnosperms, monocotyledons, and dicotyledons. Plants of interest include but are not limited to cereals such as wheat, barley, maize, triticale, etc.; fruits, such as apricots, oranges, strawberries, bananas, grapefruits, apples, pears, avocados, etc.; nuts, such as walnuts, almonds, filberts, pecans, etc.; vegetables, such as carrots, lettuce, tomatoes, celery, turnips, potatoes, broccoli, asparagus, etc.; woody species, such as poplar, pine, *sequoia*, cedar, oak, etc; ornamental flowers; or other cash crops, such as tobacco, jojoba, rapeseed, *Cuphea*, soybeans, sunflower, sugar beet and safflower.

To silence native PG activity in a fruit such as a tomato, any of several strategies may be used. The available strategies include but are not limited to the "antisense" method the "sense" or "cosuppression" method and the use of a transposable element. Two preferred methods for silencing PG expression are the "antisense" method and the "sense" or "cosuppression" method. Both of these methods may lead to silencing of the native PG activity. Sense and antisense gene regulation is reviewed by Bird and Ray in Biotechnology and Genetic Engineering Reviews 9:207–221 (1991). The use of these techniques to control selected genes in tomato has been described by Grat et al., Plant Molecular Biology, 19 69–87 (1992).

Preferably the method for silencing native PG activity is an antisense method.

The term "antisense" refers to an expressed nucleotide sequence which is complementary to, and can therefore hybridize with any one or more naturally expressed nucleotide sequences or nucleotide associated sequences of the native PG enzyme or partial sequences thereof. Because of its complementary sequence, the expressed antisense nucleotide sequence may hybridize to one or more expressed nucleotide sequences or nucleotide associated sequences (such as sense introns) of the native PG enzyme. Without wishing to be bound by theory it is believed that the expressed anti-sense nucleotide sequence of the present invention binds to expressed nucleotide sequences or nucleotide associated sequences (such as pre-mRNA) of the native PG enzyme or partial sequences thereof and thereby prevents pre-mRNA splicing and/or subsequent translation of mRNA and, therefore, PG enzyme production. The duplex nucleotide sequence complex thus formed is believed to be eventually degraded by appropriate cellular mechanisms, without resulting in expression of the native PG enzyme. This binding therefore reduces the level of plant PG enzyme activity such that the PME:PG ratio is increased and a modified pectin of relatively high molecular weight is obtained. An antisense sequence can conveniently be formed for a known protein coding region by reversing the orientation of the protein coding region so that the end that is normally transcribed last is now transcribed first.

Preferably the native PG enzyme is silenced by the in-situ expression of all or part of a nucleotide sequence encoding the native PG enzyme in an antisense orientation. In some instances expression may be silenced by PG sense expression.

In more detail, in the antisense method, a construct comprising or expressing a nucleotide sequence of the present invention which is complementary to all or part of one or more naturally expressed PG encoding nucleotide sequences or PG associated nucleotide sequences is inserted into the genome in reverse orientation and without its translation initiation signal. Without being bound by thoery, the simplest theory is that such an antisense nucleotide sequence, which expresses a nucleotide sequence which is complementary to a naturally expressed PG encoding nucleotide sequence or a PG associated nucleotide sequence binds with the naturally expressed PG encoding nucleotide sequence or a PG associated nucleotide sequence to form an entity such as a duplex which silences native PG activity.

The term "sense" refers to a nucleotide sequence which is in its natural orientation.

In one embodiment, the present invention relates to a method of affecting enzymatic activity in an organism such as a plant (or a cell, a tissue or an organ thereof) comprising expressing in the plant (or a cell, a tissue or an organ thereof) a nucleotide sequence wherein the nucleotide sequence encodes, partially or completely, an intron in a sense or antisense orientation; wherein the nucleotide sequence does not contain a sequence that is in a sense or antisense orientation to an exon sequence normally associated with the intron; and wherein PG enzyme activity is silenced such that the PME:PG ratio is increased and a modified pectin of relatively high molecular weight is obtained.

The term "intron" is used in its normal sense as meaning a segment of nucleotides, usually DNA, that does not encode part or all of an expressed protein or enzyme.

The term "exon" is used in its normal sense as meaning a segment of nucleotides, usually DNA, encoding part or all of an expressed protein or enzyme.

Thus, the term "intron" refers to gene regions that are transcribed into RNA molecules, but which are spliced out of the RNA before the RNA is translated into a protein. In contrast, the term "exon" refers to gene regions that are transcribed into RNA and subsequently translated into proteins.

Preferably the nucleotide sequence codes for at least substantially all of at least one intron in an antisense orientation.

Preferably the nucleotide sequence codes, partially or completely, for two or more introns and wherein each intron is in an anti-sense orientation.

An antisense sequence corresponding to a natural plant gene has been used to control plant biochemistry or development. By way of example, Grierson et al (1986, Nucleic Acid Reviews, 14 p 8595–8603) and EP-A2-0271 988 describe the preparation of cDNA from PG mRNA, and discloses in particular pTOM6, a plasmid containing substantially all (all but the first 20 bases) of the cDNA sequence complementary to the mRNA that is generated in the ripening tomato and that is translated into PG.

However, an antisense sequence has not been used in a process for modifying a pectin by differentially regulating the level of expression of PME and PG so that PG activity is silenced and an elevated ratio of PME to PG is obtained.

The use of an antisense method to silence PG activity is advantageous because (i) it silences PG activity by modulating PG expression in fruit such as tomatoes so that an increased ratio of PME to PG is obtained.

(ii) by silencing PG activity, elevated levels of PG free PME can be isolated and used to modify endogenous or exogenous pectin so that a modified pectin of relatively high molecular weight (50 kDa to 200 kDa is obtained).

(iii) by silencing endogenous PG activity, an in-situ reduction in molecular weight of solubilised pectin is inhibited and enhanced pectin integrity is maintained during fruit processing.

(iv) the ability to silence PG activity has a positive effect on the solids content of, for example, the tomato plant and improves tomato processing In some cases, it is not necessary that the entire nucleotide sequence of the present invention is used to silence PG activity. A smaller portion of the expressed nucleotide sequence may be sufficient to hybridize to the naturally expressed PG encoding nucleotide sequence or PG associated nucleotide sequence to silence PG activity. There is no theoretical upper limit to the nucleotide sequence—it may be as long as the relevant nucleotide sequence expressed by the cell.

Preferably the nucleotide sequence of the present invention is about 15 nucleotides in length.

Preferably the nucleotide sequence of the present invention is about 20 nucleotides in length.

Preferably the nucleotide sequence of the present invention is about 30 nucleotides in length.

Preferably the nucleotide sequence of the present invention is about 50 nucleotides in length.

Preferably the nucleotide sequence of the present invention is about 100 nucleotides in length.

Preferably the nucleotide sequence of the present invention is about 1000 nucleotides in length.

Preferably the nucleotide sequence of the present invention is about 1500 nucleotides in length.

Preferably the nucleotide sequence of the present invention is from about 100 nucleotides to about 1000 nucleotides in length.

Preferably the nucleotide sequence of the present invention is from about 150 nucleotides to about 1000 nucleotides in length.

Preferably the nucleotide sequence of the present invention is from about 100 nucleotides to about 1500 nucleotides in length.

Preferably the nucleotide sequence of the present invention is sufficiently long so that one or a few nucleotide base pairs mismatches to the naturally expressed PG encoding nucleotide sequence or PG associated nucleotide sequence will not hinder efficacy.

The nucleotide sequence of the present invention may be complementary to any sequence of the naturally expressed PG encoding nucleotide sequence or PG associated nucleotide sequence, that is, it may be proximal to the 5'-terminus or capping site, downstream from the capping site, between the capping site and the initiation codon and may cover all or only a portion of the non-coding region, may bridge the non-coding and coding region, be complementary to all or part of the coding region, complementary to the 3'-terminus of the coding region, or complementary to the 3'-untranslated region of the naturally expressed PG encoding nucleotide sequence or PG associated nucleotide sequence.

The particular site(s) to which the nucleotide sequence of the present invention binds to the naturally expressed PG encoding nucleotide sequence or PG associated nucleotide sequence and the length of the nucleotide sequence of the present invention will vary depending upon the degree of silencing desired, the uniqueness of the naturally expressed PG encoding nucleotide sequence or PG associated nucleotide sequence and the stability of the binding of the nucleotide sequence of the present invention to the naturally expressed PG encoding nucleotide sequence or PG associated nucleotide sequence.

Therefore, to some degree, these factors will be determined empirically based on the experience observed with a particular nucleotide sequence.

The nucleotide sequence of the present invention may be a single nucleotide sequence or a repetitive nucleotide sequence having two or more repetitive nucleotide sequences in tandem, where the single nucleotide sequence may bind to a plurality of naturally expressed PG encoding nucleotide sequences or PG associated nucleotide sequences. In some instances, rather than providing for homoduplexing, heteroduplexing may be employed, where the same nucleotide sequence of the present invention may provide for inhibition of a plurality of naturally expressed PG encoding nucleotide sequences or PG associated nucleotide sequences, by having regions complementary to different naturally expressed PG encoding nucleotide sequences or PG associated nucleotide sequences.

The nucleotide sequence of the present invention may be complementary to a unique naturally expressed PG encoding nucleotide sequence or PG associated nucleotide sequence so as to enhance the probability of binding. Thus, the nucleotide sequence of the present invention may be involved with the binding of a unique native PG encoding nucleotide sequence or a PG associated nucleotide sequence, a single unit of a repetitive native PG encoding nucleotide sequence or a PG associated nucleotide sequence or of a plurality of units of a repetitive PG encoding nucleotide sequences or a PG associated nucleotide sequences. The nucleotide sequence of the present invention may result in the modulation of expression of a single native PG encoding nucleotide sequence or a PG associated nucleotide sequence, or a plurality of native PG encoding nucleotide sequences or PG associated nucleotide sequences.

Silencing of naturally expressed PG encoding nucleotide sequences or PG associated nucleotide sequences using the "antisense" method is well-established in the art. It is the subject of several textbooks and many hundreds of journal publications. The principal patent reference is European Patent No. 2540,208 in the name of Calgene Inc. There is no reason to doubt the operability of the antisense method. It is well-established, used routinely in laboratories around the world and products in which it is used are on the market.

A second practical silencing technique is based on the "sense" or "co-suppression" method. Both overexpression and downregulation may be achieved by the "sense" method. If a full length copy of a naturally expressed PG encoding nucleotide sequence or PG associated nucleotide sequence is inserted into the genome then a range of phenotypes may be obtained, some overexpressing the target gene, some underexpressing. This phenomenon, which is incompletely understood, occurs at some frequency in transformed plants which have been transformed with single or multiple copies of a nucleotide sequence which may comprise a chimeric construct or additional inserted copies of a nucleotide sequence encoding a PG enzyme in the sense orientation. In many such instances, not only does the inserted PG encoding nucleotide sequence fail to express, the mechanism that suppresses expression of the inserted PG encoding nucleotide sequence also suppresses expression of the native PG encoding nucleotide sequence or a PG associated nucleotide sequence. This phenomenon has been identified in tomato, as in Fray, Plant Mol. Biol. 22:589–602 (1993), and a review discussion of this technique in general can be found in Flavell, Proc. Natl. Acad. Sci. USA, 91:3490–3496 (1994).

To use the sense or co-suppression method, a construct is made comprising, for example, the tomato PG gene in its sense, or normal transcriptional, orientation. A population of plants produced by this method may then be screened and individual phenotypes isolated. As with the antisense strategy, the inserted sequence may be lacking in a translation initiation signal. Another similarity with antisense is that the inserted sequence need not be a full length copy. Indeed, it has been found that the distribution of over- and underexpressing phenotypes is skewed in favour of underexpression and this is advantageous when silencing of the native PG encoding nucleotide sequence or a PG associated nucleotide sequence is the desired effect. The principal patent reference on the sense or cosuppression method is European Patent No. 465,572 in the name of DNA Plant Technology Inc. The sense or cosuppression method is well-established, used routinely in laboratories around the world and products in which it is used are on the market. Regardless of the transformation method, at some repeatable frequency, the resultant transformed plants will include some plants, or plant lines, with single, multiple, or tandem repeats of the inserted nucleotide sequence and, in at least a proportion of those plants, native PG activity will be silenced.

A third strategy for silencing native PG expression or activity is based on transposable elements. Transposable elements, or transposons, are genetic elements which actuate mechanisms that move themselves to different locations in a plant genome, where they insert randomly. Transposable elements have been identified which can be transferred into foreign plant species while retaining the ability to spontaneously translocate themselves. See Chuck et al., Plant Cell, 5:371–378 (1993). Since transposons insert themselves randomly into the host genome, they may disrupt the expression of a gene when they insert inside of one. One could insert such a transposon into tomato, grow many plants, and search for the inevitable plant in which the transposon has translocated into the locus of the native PG encoding nucleotide sequence or PG associated nucleotide sequence to disrupt its function. While laborious, this method would eventually result in a plant with silenced PG activity. In effect, this is a form of accelerated mutation and selection.

A fourth strategy for silencing native PG expression or activity is based on a mechanism for silencing expression or activity of a naturally expressed PG encoding nucleotide sequences or PG associated nucleotide sequence by expressing a sense or antisense intron construct for that particular PG enzyme. With the present invention, the antisense intron can be complementary to an entire intron of the PG encoding nucleotide sequence or PG associated nucleotide sequence to be silenced. However, in some circumstances, a partial sense or antisense sequence may be used (i.e. sequences that do not comprise the full complementary sequence) providing the partial sequences are capable of silencing native PG enzymatic activity. While the partial or complete nucleotide sequences of the present invention may encode an intron in a sense or antisense orientation, the partial or complete nucleotide sequence does not contain a sequence that is in a sense or antisense orientation to an exon sequence normally associated with the intron. In this way, native PG enzyme activity is silenced such that the PME:PG ratio is increased and a modified pectin of relatively high molecular weight is obtained.

In one embodiment of the present invention it is possible to silence the expression of the nucleotide sequence encoding the native PG enzyme or a PG associated nucleotide sequence or to silence native PG activity by encoding a product that inhibits the expression or activity of the native PG enzyme by expressing an antisense intron construct for that particular native PG enzyme and (e.g. at the same time) expressing a recombinant version of another enzyme or protein—in other words a nucleotide sequence of interest (NOD may be introduced such as a NOI encoding another pectin degrading enzyme such as PME. This application allows enhanced expression of desired pectin degrading enzymes such as PME in the absence of (or reduced levels of) respective native enzymes such as PG. In this way, desired pectin degrading enzymes, such as PME, can be easily separated and purified, substantially free from PG, from the host organism.

In another embodiment of the present invention it is possible to silence the expression of the nucleotide sequence encoding the native PG enzyme or a PG associated nucleotide sequence by site directed mutagenesis or to silence native PG activity by encoding a product, such as an antibody, that inhibits the expression or activity of the native PG enzyme.

The net effect of using any of these techniques, or any other effective "silencing" technique is to provide a process for modifying pectin by producing a transformed host such as a transformed plant having an elevated ratio of PME to PG. That transformed host may be a tomato plant with a silenced PG activity in the fruit. The silencing of PG activity does not itself effect overall levels of total PME activity in the fruit, but it will result in a proportionally elevated level of PME as compared to PG, which is the desired phenotype here and which can be used to modify pectin.

Preferably the native PG enzyme of the present invention comprises the amino acid sequence shown as SEQ. I.D. No.2 or a variant, derivative or homologue thereof, including combinations thereof.

Preferably, the native PG enzyme of the present invention comprises the amino acid sequence shown as SEQ. I.D. No.2, or a variant, derivative or homologue thereof.

Preferably native PG enzyme of the present invention comprises the amino acid sequence shown as SEQ. I.D. No.2.

Preferably native PG enzyme of the present invention is expressed by a nucleotide sequence comprising the nucleotide sequence shown as SEQ. I.D. No. 1 or SEQ ID No 3 or SEQ ID No 4 or a variant, derivative or homologue thereof, or combinations thereof.

Preferably native PG enzyme of the present invention is expressed by a nucleotide sequence having the nucleotide sequence shown as SEQ. I.D. No. 1 or SEQ ID No 3 or SEQ ID No 4 or a variant, derivative or homologue thereof.

Preferably native PG enzyme of the present invention is expressed by a nucleotide sequence having the nucleotide sequence shown as SEQ. I.D. No. 1 or SEQ ID No 3 or SEQ ID No 4.

Preferably, the nucleotide sequence encoding the native PG enzyme of the present invention has been prepared by use of recombinant DNA techniques.

Preferably the nucleotide sequence encoding the native PG enzyme of the present invention is silenced by all or part of a nucleotide sequence which when expressed is complementary to the naturally expressed PG encoding nucleotide sequence or a PG associated nucleotide sequence.

Preferably the nucleotide sequence encoding the native PG enzyme of the present invention has substantial homology to SEQ ID No 1 or SEQ ID No 3 or SEQ ID No 4 or a variant, homologue or derivative thereof.

The terms "variant", "homologue" or "fragment" in relation to SEQ ID No 2 of the present invention include any substitution of, variation of, modification of, replacement of, deletion of or addition of one (or more) amino acid from or to the sequence providing the resultant amino acid sequence has PG activity, preferably having at least the same activity of a PG enzyme comprising sequence shown as SEQ I.D. No. 2.

In particular, the term "homologue" covers homology with respect to structure and/or function providing the resultant enzyme has PG activity. With respect to sequence homology (i.e. similarity), preferably there is at least 75%, more preferably at least 85%, more preferably at least 90% homology to the sequence shown in the attached sequence listings. More preferably there is at least 95%, more preferably at least 98%, homology to the sequence shown in the attached sequence listings.

The terms "variant", "homologue" or "fragment" in relation to the nucleotide sequence encoding the native PG enzyme of the present invention include any substitution of, variation of, modification of, replacement of, deletion of or addition of one (or more) nucleic acid from or to the sequence providing the resultant nucleotide sequence codes for an enzyme having PG activity, preferably having at least the same activity of a native enzyme comprising the sequence shown as SEQ I.D. No. 2. In particular, the term "homologue" covers homology with respect to structure and/or function providing the resultant nucleotide sequence encodes a native enzyme having PG activity. With respect to sequence homology (i.e. similarity), preferably there is at least 75%, more preferably at least 85%, more preferably at least 90% homology. More preferably there is at least 95%, more preferably at least 98%, homology.

In a preferred aspect, the terms "variant", "homologue" or "fragment" in relation to the nucleotide sequence encoding the PG enzyme of the present invention include any substitution of, variation of, modification of, replacement of, deletion of or addition of one (or more) nucleic acid from or to the sequence sequence shown as SEQ I.D. No. 1 or SEQ ID No 3 or SEQ ID No 4 providing the resultant nucleotide sequence encodes an enzyme having PG activity, preferably having at least the same activity of a PG enzyme comprising the sequence shown as SEQ I.D. No. 2.

In particular, the term "homologue" covers homology with respect to structure and/or function providing the resultant nucleotide sequence codes for an enzyme having PG activity. With respect to sequence homology (i.e. similarity), preferably there is at least 75%, more preferably at least 85%, more preferably at least 90% homology. More preferably there is at least 95%, more preferably at least 98%, homology.

The above terms are synonymous with allelic variations of the sequences.

As indicated above, the present invention concerns the sequence presented in the attached sequence listings, or a variant, derivative or homologue thereof.

Preferably, the variant, derivative or homologue can have at least 75% sequence homology (i.e. identity) with any one or more of the sequences presented.

In particular, the term "homology" as used herein may be equated with the term "identity".

Here, sequence homology can be determined by a simple "eyeball" comparison of any one or more of the sequences with another sequence to see if that other sequence has at least 75% identity to the sequence(s).

Relative sequence homology (i.e. sequence identity) can also be determined by commercially available computer programs that can calculate % homology between two or more sequences. A typical example of such a computer program is CLUSTAL.

Sequence homology (or identity) may moreover be determined using any suitable homology algorithm, using for example default parameters. Advantageously, the BLAST algorithm is employed, with parameters set to default values. The BLAST algorithm is described in detail at http://www.ncbi.nih.gov/BLAST/blast$_{13}$help.html, which is incorporated herein by reference. The search parameters are defined as follows, and are advantageously set to the defined default parameters.

Advantageously, "substantial homology" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (see http://www.ncbi.nih.gov/BLAST/blast_help.html) with a few enhancements. The BLAST programs were tailored for sequence similarity searching, for example to identify homologues to a query sequence. The programs are not generally useful for motif-style searching. For a discussion of basic issues in similarity searching of sequence databases, see Altschul et al (1994) Nature Genetics 6:119–129.

The five BLAST programs available at http://www.ncbi.nlm.nih.gov perform the following tasks:

blastp compares an amino acid query sequence against a protein sequence database;

blastn compares a nucleotide query sequence against a nucleotide sequence database;

blastx compares the six-frame conceptual translation products of a nucleotide query sequence (both strands) against a protein sequence database;

tblastn compares a protein query sequence against a nucleotide sequence database dynamically translated in all six reading frames (both strands).

tblastx compares the six-frame translations of a nucleotide query sequence against the six-frame translations of a nucleotide sequence database.

BLAST uses the following search parameters:

HISTOGRAM Display a histogram of scores for each search; default is yes. (See parameter H in the BLAST Manual).

DESCRIPTIONS Restricts the number of short descriptions of matching sequences reported to the number specified; default limit is 100 descriptions. (See parameter V in the manual page). See also EXPECT and CUTOFF.

ALIGNMENTS Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

EXPECT The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

MATRIX Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND Restrict a TBLASTN search to just the top or bottom strand of the database sequences; or restrict a BLASTN, BLASTX or TBLASTX search to just reading frames on the top or bottom strand of the query sequence.

FILTER Mask off segments of the query sequence that have low compositional complexity, as determined by the SEG program of Wootton & Federhen (1993) Computers and Chemistry 17:149–163, or segments consisting of short-periodicity internal repeats, as determined by the XNU program of Claverie & States (1993) Computers and Chemistry 17:191–201, or, for BLASTN, by the DUST program of Tatusov and Lipman (see http://www.ncbi.nlm.nih.gov). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNNN" and the letter "X" in protein sequences (e.g., "XXXXXXXXX").

Filtering is only applied to the query sequence (or its translation products), not to database sequences. Default filtering is DUST for BLASTN, SEG for other programs. It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi Causes NCBI gi identifiers to be shown in the output, in addition to the accession and/or locus name.

Most preferably, sequence comparisons are conducted using the simple BLAST search algorithm provided at http://www.ncbi.nlm.nih.gov/BLAST.

Other computer program methods to determine identity and similarity between the two sequences include but are not limited to the GCG program package (Devereux et al 1984 Nucleic Acids Research 12: 387 and FASTA (Atschul et al 1990 J Molec Biol 403–410).

The present invention also encompasses nucleotide sequences that are capable of hybridising to the sequences presented herein, or any derivative, fragment or derivative thereof.

The present invention also relates to nucleotide sequences that are complementary to sequences that can hybridise to the nucleotide sequences of the present invention (including complementary sequences of those presented herein).

The present invention also encompasses nucleotide sequences that are capable of hybridising to the sequences that are complementary to the sequences presented herein, or any derivative, fragment or derivative thereof.

The term "complementary" also covers nucleotide sequences that can hybridise to the nucleotide sequences of the native PG encoding nucleotide sequence.

The term "variant" also encompasses sequences that are complementary to sequences that are capable of hydridising to the nucleotide sequences presented herein.

Preferably, the term "variant" encompasses sequences that are complementary to sequences that are capable of hydridising under stringent conditions (eg. 65° C. and 0.1×SSC {1×SSC=0.15 M NaCl, 0.015 Na$_3$ citrate pH 7.0}) to the nucleotide sequences presented herein.

The term "hybridization" as used herein shall include "the process by which a strand of nucleic acid joins with a complementary strand through base pairing" (Coombs J (1994) Dictionary of Biotechnology, Stockton Press, New York N.Y.) as well as the process of amplification as carried out in polymerase chain reaction technologies as described in Dieffenbach C W and GS Dveksler (1995, PCR Primer, a Laboratory Manual, Cold Spring Harbor Press, Plainview N.Y.).

Also included within the scope of the present invention are nucleotide sequences that are capable of hybridizing to the nucleotide sequences presented herein under conditions of intermediate to maximal stringency. Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical nucleotide sequences while an intermediate (or low) stringency hybridization can be used to identify or detect similar or related nucleotide sequences.

In a preferred aspect, the present invention covers nucleotide sequences that can hybridise to the nucleotide sequence of the present invention under stringent conditions (e.g. 65° C. and 0.1×SSC).

In addition to the sequences presented in the attached sequence listings (as well as fragments, derivatives or homologues thereof), the present invention also covers sequences that are complementary to the aforementioned sequence listings (as well as fragments, derivatives or homologues thereof). The present invention also covers sequences that can hybridise to the aforementioned sequence listings (as well as fragments, derivatives or homologues thereof). The present invention also covers sequences that are complementary to sequences that can hybridise to the aforementioned sequence listings (as well as fragments, derivatives or homologues thereof). If the sequence is complementary to a fragment thereof then that sequence can be used a probe to identify similar coding sequences in other hosts.

In addition to the nucleotide sequence of the present invention, the construct of the present invention also comprises a promoter capable of expressing a nucleotide sequence complementary to a naturally expressed PG encoding nucleotide sequence or a PG associated nucleotide sequence and a 3' termination sequence.

The term "promoter" is used in the normal sense of the art, e.g. an RNA polymerase binding site.

Preferably the promoter is functional in a plant.

A large number of promoters are available which are functional in plants. These promoters may be obtainable from Ti- or Ri-plasmids, from plant cells, plant viruses or other hosts where the promoters are found to be functional in plants. Examples of promoters of bacterial origin functional in plants include but are not limited to the octopine synthetase promoter, the nopaline synthase promoter, and the manopine synthetase promoter. Viral promoters include but are not limited to the cauliflower mosaic virus full length (35S) and region VI promoters. Endogenous plant promoters include but are not limited to the ribulose-1,6-biphosphate (RUBP) carboxylase small subunit (ssu), the β-conglycinin promoter, the phaseolin promoter, the ADH promoter, heat-shock promoters and tissue specific promoters such as promoters associated with fruit ripening.

The promoter region may comprise a regulatory region which may be a naturally-occurring region, a RNA polymerase binding region freed of the regulatory region, or a combination of an RNA polymerase binding region from one gene and regulatory region from a different gene. The regulatory region may be responsive to a physical stimulus, such as heat, with heat shock genes, or light, such as with RUBP carboxylase SSU. Alternatively, the regulatory region may be sensitive to differentiation signals, such as but not limited to the β-conglycinin gene and the phaseolin gene. A third type of regulatory region is responsive to metabolites. The time and level of expression of a nucleotide sequence complementary to a naturally expressed PG encoding nucleotide sequence or a PG associated nucleotide sequence may have a definite effect on the phenotype produced. Thus the promoters chosen may determine the silencing effect of an antisense nucleotide sequence complementary to a naturally expressed PG encoding nucleotide sequence or a PG associated nucleotide sequence.

The choice of promoter may provide for constitutive expression or regulated expression. The promoter region may comprise a regulatory region which is desirably inducible, rather than constitutive, particularly being active at the time of fruit breaking (shortly prior to ripening). For this purpose the promoter associated with the native PG encoding nucleotide sequence may be employed or a promoter of another nucleotide encoding sequence associated with the development of fruit during ripening. In another aspect, the nucleotide sequence according to the present invention may under the control of a promoter that may be a cell or tissue specific promoter. If, for example, the host is a plant then the promoter can be one that affects expression of the nucleotide sequence in any one or more of tuber, stem, sprout, root and leaf tissues.

Preferably the promoter is the promoter associated with the native PG encoding nucleotide sequence.

The promoter could additionally include features to ensure or to increase expression in a suitable host. For example, the features can be conserved regions such as a TATA box. The promoter may even contain other sequences to affect (such as to maintain, enhance, decrease) the levels of expression of the nucleotide sequence of the present invention or, in the case of the combination of constructs, an NOI. For example, suitable other sequences include the Sh1-intron or an ADH intron. Also, suitable elements to enhance transcription or translation may be present. An example of the latter element is the TMV 5' signal sequence (see Sleat Gene 217 [1987] 217–225; and Dawson Plant Mol. Biol. 23 [1993] 97).

By way of example, the promoter for the nucleotide sequence of the present invention can be the α-Amy 1 promoter (otherwise known as the Amy 1 promoter, the Amy 637 promoter or the α-Amy 637 promoter) as described in WO 96/12813. Alternatively, the promoter for the nucleotide sequence of the present invention can be the α-Amy 3 promoter (otherwise known as the Amy 3 promoter, the Amy 351 promoter or the α-Amy 351 promoter) as described in WO96/12814.

The present invention also encompasses the use of promoters to express a nucleotide sequence according to the present invention or the NOI of the present invention wherein a part of the promoter is inactivated but wherein the promoter can still function as a promoter. Partial inactivation of a promoter in some instances is advantageous. In particular, with the Amy 351 promoter mentioned earlier it is possible to inactivate a part of it so that the partially inactivated promoter expresses the nucleotide of the present invention or an NOI in a more specific manner such as in just one specific tissue type or organ.

The term "inactivated" means partial inactivation in the sense that the expression pattern of the promoter is modified but wherein the partially inactivated promoter still functions as a promoter. However, as mentioned above, the modified promoter is capable of expressing the nucleotide sequence of the present invention or an NOI in at least one (but not all) specific tissue of the original promoter. One such promoter is the Amy 351 promoter described above. Examples of partial inactivation include altering the folding pattern of the promoter sequence, or binding species to parts of the nucleotide sequence, so that a part of the nucleotide sequence is not recognised by, for example, RNA polymerase. Another, and preferable, way of partially inactivating the promoter is to truncate it to form fragments thereof. Another way would be to mutate at least a part of the sequence so that the RNA polymerase can not bind to that part or another part. Another modification is to mutate the binding sites for regulatory proteins for example the CreA protein known from filamentous fungi to exert carbon catabolite repression, and thus abolish the catabolite repression of the native promoter.

Any convenient termination region may be employed, conveniently the termination region of the RNA polymerase binding region, or a different termination region. Various termination regions are available and the choice is primarily one of convenience, where prior constructions or DNA sequences may be available. Conveniently, the opine termination regions may be employed, or termination regions from native PG enzymes.

In addition the present invention also encompasses combinations of promoters and/or nucleotide sequences and/or elements and/or combinations of constructs comprising one or more NOIs.

The term "NOI" with reference to the combination of constructs according to the present invention means any nucleotide sequence of interest. An NOI can be any nucleotide that is either foreign or natural to the host (e.g. filamentous fungus, preferably of the genus *Aspergillus*, or a plant) in question. Typical examples of an NOI include nucleotide sequences encoding for proteins and enzymes that modify metabolic and catabolic processes. The NOI may encode an agent for introducing or increasing pathogen resistance. The NOI may even comprise a construct for modifying the expression of natural transcripts present in the relevant tissues. The NOI may even encode a non-native protein of a filamentous fungus, preferably of the genus *Aspergillus*, or a compound that is of benefit to animals or humans.

Examples of NOIs include other pectinolytic enzymes, pectin depolymerases, PMEs, pectate lyases, pectin lyases, rhamno-galacturonases, hemicellulases, endo-β-glucanases, arabinases, or acetyl esterases, or combinations thereof, as well as antisense sequences thereof.

The NOI can be a PME as disclosed in WO-A-97/03574 or the PME disclosed in either WO-A-94/25575 or WO-A-97/31102 as well as variants, derivatives or homologues of the sequences disclosed in those patent applications.

The NOI may be a protein giving nutritional value to a food or crop. Typical examples include plant proteins that can inhibit the formation of anti-nutritive factors and plant proteins that have a more desirable amino acid composition (e.g. a higher lysine content than a non-transformed plant). The NOI may even encode an enzyme that can be used in food processing such as chymosin, thaumatin and α-galactosidase. The NOI can be a gene encoding for any one of a pest toxin, an antisense transcript such as that for patatin or α-amylase, ADP-glucose pyrophosphorylase (e.g. see EP-A-0455316), a protease antisense, a glucanase or a native/endogenous PME.

In one embodiment of the present invention, a combination of constructs may be used. By way of example, a first NOI may comprise a construct comprising or expressing a nucleotide sequence capable of silencing a naturally expressed PME encoding nucleotide sequence or a PME associated nucleotide sequence or by encoding a product that silences native PME expression or PME activity, and a second NOI which may comprise a construct comprising or expressing a nucleotide sequence encoding a PME such as an exogenous PME encoding nucleotide sequence such as that from *Erwinia* (as described in UK Patent Application number 9820195.7) or orange fruit.

By way of example, the NOI may even encode an intron of a particular enzyme but wherein the intron can be in a sense or antisense orientation. In the latter instance, the particular enzyme could be native PME. Antisense expression of native exon or intron sequences as the NOI would mean that the natural PME expression would be reduced or eliminated but wherein recombinant PME expression would not be affected. This is particularly true for antisense intron or sense intron expression.

In the case of the combination of constructs, an NOI may be directly or indirectly attached to a promoter. An example of an indirect attachment is the provision of a suitable spacer group such as an intron sequence, such as the Sh1-intron or the ADH intron, intermediate between the promoter and the nucleotide sequence of the present invention or the NOI. The same is true for the term "fused" in relation to the present invention which includes direct or indirect attachment. In each case, the terms do not cover the natural combination of the NOI coding for the enzyme ordinarily associated with the wild type gene promoter and when they are both in their natural environment.

As indicated above, a preferred transformed host is a transformed plant or plant tissue or plant cell. In this respect, the constructs and/or combinations of constructs of the present invention may be inserted into the genome of the target plant species by transformation, followed by regeneration of the transformants into whole plants. Transformation methods exist for most plant species or can be obtained by adaptation of available methods.

EP-B-0470145 and CA-A-2006454 provide some useful background commentary on the types of techniques that may be employed to prepare transformed plants according to the present invention. Some of these background teachings are now included in the following commentary.

The basic principle in the construction of genetically modified plants is to insert genetic information in the plant genome so as to obtain a stable maintenance of the inserted genetic material.

Preferably, the vector system is an *Agrobacterium tumefaciens* Ti-plasmid or an *Agrobacterium rhizogenes* Ri-plasmid or a derivative thereof.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27).

For dicotyledonous plants the most widely used vector method is *Agrobacterium*-mediated transformation which is based on the use of a Ti plasmid from *Agrobacterium tumefaciens* or a Ri plasmid from *Agrobacterium rhizogenes* An et al. (1986), *Plant Physiol.* 81, 301–305 and Butcher D. N. et al. (1980), *Tissue Culture Methods for Plant Pathologists*, eds.: D. S. Ingrams and J. P. Helgeson. 203–208. The rhizobacterium *Agrobacterium tumefaciens*, or the related *Agrobacterium rhizogenes*, contain plasmids which, in nature, cause the formation of disease symptoms, crown gall of hair root tumours, in plants which are infected by the bacterium. Part of the mechanism employed by *Agrobacterium* in pathogenesis is that a section of plasmid DNA which is bounded by right and left border regions is transferred stably into the genome of the infected plant. Therefore, if foreign DNA is inserted into the so-called "transfer" region (T-region) in substitution for the genes normally present therein, that foreign gene will be transferred into the plant genome. Preferably the construct will include one T-DNA border, particularly the right T-DNA border, or may be sandwiched between the left and right T-DNA borders. The nucleotide sequence or construct of the present invention is preferably inserted into the Ti-plasmid between the terminal sequences of the T-DNA or adjacent a T-DNA sequence so as to avoid disruption of the sequences immediately surrounding the T-DNA borders. Several different Ti and Ri plasmids have been constructed which are suitable for the construction of the plant or plant cell constructs described above. A non-limiting example of such a Ti plasmid is pGV3850. There are many hundreds of references in the journal literature, in text books and in patents and the methodology is well-established.

In the construction of a transformed plant the nucleotide sequence or construct of the present invention may be first constructed in a microorganism in which the vector can replicate and which is easy to manipulate before insertion into the plant. An example of a useful microorganism is *E. coli*., but other microorganisms having the above properties may be used. By way of example, as reported in CA-A-2006454, a large amount of cloning vectors are available which contain a replication system in *E. coli* and a marker which allows a selection of the transformed cells. The vectors may contain for example pBR 322, the pUC series, the M13 mp series or pACYC 184.

The *E. coli* cells are cultivated in a suitable nutrient medium and then harvested and lysed. The plasmid is then recovered. As a method of analysis there is generally used sequence analysis, restriction analysis, electrophoresis and further biochemical-molecular biological methods. After each manipulation, the used DNA sequence can be restricted and connected with the next DNA sequence. Each sequence can be cloned in the same or different plasmid.

The term "transformation vector" means a construct capable of being transferred from one species to another—such as from an *E. coli* plasmid to a plant. It may also be a construct capable of being transferred from an *E. coli* plasmid to a plant or to an *Agrobacterium* to a filamentous fungus, preferably of the genus *Aspergillus*.

The vector system may comprise one vector, but it can comprise two vectors. In the case of two vectors, the vector system is normally referred to as a binary vector system. Binary vector systems are described in further detail in Gynheung An et al. (1980), Binary Vectors, *Plant Molecular Biology Manual A*3, 1–19.

By having a marker as part of the expression construct, particularly antibiotic resistance, such as but not limited to kanamycin resistance, hygromycin resistance, gentamicin resistance and bleomycin resistance, one can select for those plant cells which have retained the construct in functional form. Where binary vectors are being employed and where the T-DNA in the Ti- or Ri-plasmid of the *Agrobacterium* retains the oncogenes, one will select for morphologically normal cells, which lack oncogenic expression.

Direct infection of plant tissues by *Agrobacterium* is a simple technique which has been widely employed and which is described in Butcher D. N. et al. (1980), *Tissue Culture Methods for Plant Pathologists*, eds.: D. S. Ingrams and J. P. Helgeson, 203–208. For further teachings on this topic see Potrykus (Annu Rev Plant Physiol Plant Mol Biol [1991] 42:205–225) and Christou (Agro-Food-Industry Hi-Tech March/April 1994 17–27). With this technique, infection of a plant may be done on a certain part or tissue of the plant. i.e. on a part of a leaf, a root, a stem or another part of the plant.

Typically, with direct infection of plant tissues by *Agrobacterium* comprising the construct of the present invention, a plant to be infected is wounded, e.g. by cutting the plant with a razor or puncturing the plant with a needle or rubbing the plant with an abrasive. The wound is then inoculated with the *Agrobacterium*. The inoculated plant or plant part is then grown on a suitable culture medium and allowed to develop into mature plants.

The effectiveness of *Agrobacterium* is restricted to the host range of the microorganism and is thus restricted more or less to dicotyledonous plant species. In general monocotyldonous species, which include the important cereal crops, are not amenable to transformation by the *Agrobacterium* method. However, various methods for the direct insertion of DNA into the nucleus of monocot cells are known.

By way of example, in the ballistic method, microparticles of dense material, usually gold or tungsten, are fired at high velocity at the target cells where they penetrate the cells, opening an aperture in the cell wall through which DNA may enter. The DNA may be coated on to the microparticles or may be added to the culture medium. Accelerated particle transformation of the tomato plant is possible.

One particle bombardment technique that can be performed uses the Particle Inflow Gun (PIG), which was developed and described by Finer et al. [1992] and Vain et al. [1993]. The PIG accelerates the micro-projectiles in a stream of flowing helium, through a partial vacuum, into the plant cells.

One of advantages of the PIG is that the acceleration of the micro-projectiles can be controlled by a timer-relay solenoid and by regulation the provided helium pressure. The use of pressurised helium as a driving force has the advantage of being inert, leaves no residues and gives reproducible acceleration. The vacuum reduces the drag on the particles and lessens tissue damage by dispersion of the helium gas prior to impact [Finer et al. 1992].

Another method includes microinjection whereby the DNA is inserted by injection into individual cells via an ultrafine hollow needle.

Another method, applicable to both moncots and dicots, involves creating a suspension of the target cells in a liquid, adding microscope needle-like material, such as silicon carbide or silicon nitride "whiskers" and agitating so that the cells and whiskers collide and DNA present in the liquid enters the cell.

Another transformation method that has been proven effective in tomatoes is electroporation of protoplasts.

Thus, in one aspect, the present invention relates to a vector such as an *Agrobacterium* system comprising a nucleotide sequence and/or construct according to the present invention and which is capable of introducing the nucleotide sequence and/or construct into the genome of an host of the present invention such as a plant.

When plant cells are constructed, these cells may be grown and maintained in accordance with well-known tissue culturing methods such as by culturing the cells in a suitable culture medium supplied with the necessary growth factors such as amino acids, plant hormones, vitamins, etc. Regeneration of the transformed cells into transformed plants may be accomplished using known methods for the regeneration of plants from cell or tissue cultures, for example by selecting transformed shoots using an antibiotic and by subculturing the shoots on a medium containing the appropriate nutrients and/or plant hormones. By way of example, calli can be developed from the cells and the calli induced to form shoots which may then be transfered to an appropriate nutrient medium in soil to regenerate the plant. The plants will then grow and, as appropriate, may be crossed with other plants so as to establish the stability of the change in phenotype over a number of generations. Other techniques may be employed for regenerating the plants without pollination or fertilization. Because those plant genotypes that can be regenerated from culture may not be directly applicable as crop varieties, the transformed plant may be crossed with alternate untransformed germplasm in order to transfer the trait to appropriate breeding lines.

Further teachings on plant transformation may be found in EP-A-0449375.

The process of the present invention can occur ex vivo or even in vivo—such as in planta. In the latter respect, the plant may be a transformed plant, such as a plant that has been modified to produce different levels and/or types of pectin. The plant may also be plant material, rather than a whole plant. Here, the plant material may be obtained from a transformed plant, such as a plant that has been modified to produce different levels and/or types of pectin. The plant or plant material may be or may be derived from a vegetable, a fruit, or other type of pectin containing or producing plant. Here, the vegetable material and/or the fruit material can be a mash.

The present invention will now be described only by way of example, in which reference is made to the following attached FIGURE:

FIG. 1 provides the nucleotide sequence for PG cDNA clone (pTOM6) (SEQ ID No 1).

EXPERIMENTAL SECTION

Methods I

1. Creation of a cDNA Library

A cDNA library was prepared using a commercially available kit (Stratagene, LaJolla, Calif.) with RNA obtained from red tomatoes. Mature fruit tissue was collected from greenhouse grown tomato plants and frozen with liquid nitrogen. Total RNA was extracted via the following method: Ten grams of frozen tissue was ground to a powder in liquid nitrogen with a mortar and pestle and homogenized with a polytron in 20 ml of lysis buffer [8M guanidine thiocyanate, 10 mM EDTA, 300 mM Tris-Hcl (pH 7.6), 8% b-mercaptoethanol]. Following centrifugation at 3,000 g for 10 minutes, the supernatant was filtered through miracloth and extracted twice with phenol/chloroform and once with chloroform. RNA was ethanol precipitated and the resulting pellet was washed with 3.0M sodium acetate (pH 5.5), then dissolved in 10 mM Tris, pH 7.6; 1 mM EDTA; 1% SDS and reprecipitated with 2.5M LiCl (Sambook, et al, Molecular Cloning Manual, Cold Spring Harbor, 1989).

2. Preparation of Probes for Screening the cDNA Library

Purification and Characterisation of the PG Enzyme

This cDNA library was screened with probes prepared from peptide fragments of the PG enzyme. The fragments were obtained in the following way: Ripe pericarp tissue was homogenized in ice-cold distilled $H_2O$ at a ratio of 1 kg fruit to 1 liter water and the resulting slurry adjusted to pH 3.0. Cell debris was pelleted by centrifugation at 10,000 g for 20 minutes, resuspended in one half volume of cold $H_2O$ at pH 3.0 and repelleted.

The cell debris pellet was resuspended in cold buffer contained 50 mM sodium acetate, 1.25M NaCl (pH 6.0) and stirred for at least one hour at 4° C. The extract was centrifuged at 10,000 g for 20 minutes and proteins in the supernatant were precipitated by the addition of ammonium sulfate to 70% saturation. After centrifugation, the resulting protein pellet was resuspended in 0.125M sodium acetate (pH 6.0) and dialyzed extensively against the same buffer. The dialyzed extract was then clarified by centrifugation and applied to a CM-Sepharose column equilibrated with 0.125M sodium acetate (pH 6.0). Bound proteins were eluted by a two step gradient of 0.45M sodium acetate (pH 6.0) and 1.0M sodium acetate (pH 6.0).

The 1.0M sodium acetate eluent was concentrated by ultrafiltration, dialyzed against Concanavalin A (Con-A) buffer [500 mM NaCl, 50 mM sodium acetate, 1 mM calcium acetate, 1 mM manganese sulfate (pH 6.0)] and further purified by Con-A chromatography. PG-containing fractions were concentrated by ultrafiltration, dialyzed against 50 mM phosphate, 200 mM NaCl, 0.1 mM DDT (pH 6.0) and further purified by Mono S FPLC chromatography, Pogson et al, Aust. J. Plant Phys. 18:65–79 (1991).

PG purification and separation was followed by SDS-PAGE. Electrophoretic blotting, and detection methods for the catalytic PG polypeptide are performed. PG levels during extraction and purification were determined as described below (see page 50).

Nucleotide Sequence Analysis and Preparation of Probes/Primers

N-terminal sequence analysis of the purified PG enzyme was performed with an Applied Biosystems 476A protein sequenator.

Internal PG proteolytic fragments were generated by digestion with Lys-C and Glu-C endoproteases following instructions supplied by the manufacturer (Promega, Madison, Wis.). The resulting proteolytic fragments were resolved by SDS-PAGE, blotted to PVDF membranes and directly sequenced.

Two internal peptide fragments were of interest. The amino acid sequence of the Lys-C peptide was:
$NH_2$-Asn-Gly-Asn-Gly-Ala-Asn-Gly-Gln-[?]-Val (SEQ ID NO: 5).

The amino acid sequence of the Glu-C peptide was:
$NH_2$-Ala-Asn-Ala-Gly-Asp-Gln-Tyr (SEQ ID NO: 6).

From these sequences a nucleotide primer was constructed.

These nucleotide primers are presented as:
GGNAAYGGNG CNAAYGG SEQ ID NO: 7 (for the Lys-C primer) and
AAYGCNGGNG AYCARTA SEQ ID No 8 (for the Glu-C primer).

PCR Generation of cDNA Probes for cDNA Library Screening

These degenerate oligonucleotides were used for library screening and PCR-based generation of cDNA probes. One microgram of poly (A)+ RNA from fully ripe tomato pericarp tissues was used in PCR reactions. A Not I primer-adaptor (Promega, Madison, Wis.) was used as a primer for first strand cDNA synthesis. Subsequent PCR amplification cycles utilized a Not I adaptor as the 3' primer and a degenerate 5' primer (SEQ ID NO: 8), derived from the Glu-C protease fragment. Amplified products were electrophoresed, blotted to nylon membranes and probed with a second degenerate oligonucleotide (SEQ ID NO: 7) derived from the Lys-C PG protease fragment. The Lys-C primer recognized a 1.3 kb product generated in the pcr reactions. This 1.3 kb product was recovered and amplified by PCR using the Lys-C primer (5'-end) and the Not I adaptor (3'-end). This second 1.25 kb PCR product was used in conjunction with degenerate oligonucleotides for library screening and Northern analysis. Oligonucleotide 5'-end labelling and random primer DNA labelling were performed following the manufacturer's protocol (BRL, Gaithersburg, Md.).

3. cDNA Library Screening Procedure

The cDNA library contained $1.0 \times 10^7$ individual recombinants before amplification. For primary screening, replica nitrocellulose filters (25.000 pfu/plate) were probed with the degenerate 17-mer Lys-C oligonucleotide described above. Prehybridization was carried out for 4 hours at 37° C. in a solution of 6×SSC; 1×Denhardt's solution; 0.5% SDS; 0.05% sodium pyrophosphate; 100 µg/ml denatured salmon sperm DNA. Hybridization was carried out overnight at 37° C. in 6×SSC; 1×Denhardt's solution; 20 µg/ml tRNA; 0.05% sodium pyrophosphate. Following hybridization, the filters were washed twice for 5 minutes at room temperature and twice at 37° C. for 30 minutes in 5×SSC; 0.05% sodium pyrophosphate. A final wash was performed in 5×SSC; 0.05% sodium pyrophosphate at 40° C. for 10 minutes. The filters were exposed overnight with intensifying screens at −80° C.

Further rounds of screening were performed at low density using the PCR-generated cDNA fragment (described above), the Glu-C oligonucleotide and a degenerate N-terminal oligonucleotide [5'-AT(AG) TCX CC(AG) CT(GA) TG(CT) TT(CT) TC (SEQ ID NO: 9)] derived from the N-terminal protein sequence. Hybridization conditions for these oligonucleotides were as described above. Hybridization conditions used with the cDNA fragments were as described by Sambook et al 1989, (ibid). Following plaque purification, plasmids were rescued by in vivo excision, following the manufacture's protocol (Stratagene). Double-stranded DNA sequencing was performed.

SEQ ID NO: 4 is the consensus DNA sequence obtained from the clones.

4. Antisense Expression of PG cDNA Nucleotide Sequence

Expression of the native PG enzyme may be silenced by introducing Cauliflower Mosaic Virus (CaMV) 35S promoter driven chimeric genes containing a full-length PG cDNA in the antisense orientation into various tomato genotypes. This highly expressed constitutive promoter is widely available. Other promoters may also be utilized. The constitutive CaMV 35S promoter may be initially used for the proposed experiments because this promoter has been shown to promote high levels of protein production in most plant organs, including tomato fruit.

A similar strategy to Kramer, et al. (Horticultural Biochemistry 1990: 347–355) may be employed to inhibit expression of the PG protein in transgenic tomato plants. Antisense silencing of PG enzyme production will greatly decrease the amount of PG enzyme available thereby resulting in an accumulation of the PME enzyme and an elevation in the PME to PG ratio.

First, an antisense construct may be created. At a minimum, this construct contains a promoter effective to promote expression in fruits, an antisense sequence of the cDNA clone encoding the PG enzyme and a sequence effective to terminate transcription. Via standard molecular biological methods, the CaMV35S promoter sequence may be attached to the PG cDNA insert. The cDNA insert is in an antisense orientation. This orientation may be accomplished by attaching the 3' end of the PG cDNA insert to the promoter.

A suitable termination sequence, such as the nopaline synthase 3' terminator may be placed downstream from the cDNA insert.

The DNA construction will be placed in an appropriate vector for plant transformation. For *Agrobacterium*-mediated transformation, the promoter/cDNA/terminator construction will preferably be placed in a Ti-based plasmid, such as pBI121, a standard binary vector.

In general, transformation is carried out with two standard *Agrobacterium* binary vectors: pBI121 (sold by Clontech Laboratories, Palo Alto Calif.) and pGA643 (developed by G. An at Washington State University). pBI121 contains a CAMV promoter and GUS reporter gene. The GUS coding sequence may be removed by digesting with SstI and SmaI (blunt end). The PG cDNA fragment may be produced by digesting with SstI (sticky end) and NruI (blunt end). The sticky/blunt ends allow for directional cloning into pBI121 in the antisense orientation. Standard methods for cutting, ligating and *E. coli* transformation are used.

For plant transformation the methods of McCormick (1986, Plant Cell Reporter 5:81–84) and Plant Tissue Culture Manual B6:1–9 (1991) Kluwer Academic Publishers are used. This reference compiles/compares various procedures for *Agrobacterium*-mediated transformation of tomato.

The levels of native PG activity and PME activity may then be analyzed. Fruit from transgenic antisense tomatoes may be processed to assess levels of PG activity. If the ratio of PG to PME is less than the wild type, then the effort is deemed to have been successful.

5. Construction of Antisense and Sense Plant Expression Constructs and Plant Transformation The PG encoding DNA sequence as set forth in SEQ ID No 4 was inserted into a plasmid vector. Copies of a plant binary vector pBI121 were purchased (Clontech). The vector pBI121 comprises a plant expression construct including a plant expressible constitutive promoter, the cauliflower mosaic virus 35S promoter, followed by nucleotide sequence encoding the enzyme beta glucuronidase (GUS), followed, in turn, by a polyadenylation signal from the nopaline synthase gene. In essence, the GUS coding region was excised from pBI121 and replaced with the PG encoding nucleotide sequence in both sense and antisense orientations.

For the antisense construction, the plasmid vector comprising SEQ ID No 4 was digested with NruI and Sst 1. This digestion frees a 1852 base pair fragment. The NruI site is at base pair 1792 in SEQ ID No 4 while the SstI site in the plasmid vector is before the cDNA insert of SEQ ID No 4. Separately, pBI121 was digested with SmaI (blunt end) and Sst 1 (5' overhang) to remove the GUS coding region from the vector. After size separation from unwanted fragments on agarose gels, the two desired fragments were ligated with ligase (BRL), and the resultant vectors transformed into XL-1 Blue bacteria. The antisense construction was designated pBant18.

For the sense orientation, the plasmid vector cDNA clone was digested with KpnI and XbaI, and the resulting 2053 base pair fragment was sub-cloned into the KpnI-XbaI site of pUC19, to create a plasmid designated pBsen20. The KpnI site is at base pair 2009 in SEQ ID No 4 and the XbaI site is again beyond base pair 1 in the host vector. The purified pBsen20 was then digested with SstI and XbaI the smaller fragment was recovered from a LMA gel, and then the fragment was ligated into pBI121 previously cut with XbaI and SstI to remove the GUS coding region. The resulting plasmid, designated pBsen20 was also transformed into XL-1 Blue bacteria.

Copies of both pBant18 and pBsen20 were then transferred into *Agrobacterium tumefaciens* by the tri-parental technique. The *Agrobacterium* culture (LBA 4404) was grown on an M9 sucrose liquid medium without antibiotics at 28° C. Colonies of *E. coli*, (containing both pBant18 and pBsen20, as well as helper plasmid pRK2013) were streaked on LB plates under kanamycin selection (50 ug/ml) at 37° C. and then cultured in 3 ml of LB liquid medium without antibiotics. 50 ul of each of the three cultures (LBA4404, pRK2013, and the sense or antisense construction) were combined on LB plates without antibiotics to be cultured overnight at 28° C. The resultant culture was placed in 2 ml of LB liquid medium with both kanamycin (50 ug/ml) and streptomycin (250 ug/ml), and cultured overnight with shaking. Minipreps were used to verify correct constructs.

Dry tomato seeds of variety Ailsa Craig were sterilized, plated, and placed in a growth chamber for 10 to 14 days. The tops of the seedlings were cut, taking the top half of the hypocotyl as well as the cotyledons, and floated in liquid MSO. Cotyledons were cut, placed on a filter paper disk over tobacco feeder cells and cultured in a growth chamber overnight. The cotyledons were removed, plated and inoculated with the *Agrobacterium* harboring the genetic construction. After 48 hours of co-cultivation, the cotyledons were re-plated in D1 medium with kanamycin (25 ug/ml) and cefotaxime (100 ug/ml). Callus grew on some treated cotyledons, and the callus was sub-cultured in D2 medium with kanamycin (25 ug/ml) and cefotaxime (100 ug/ml) for shoot organogenesis. After three weeks, shoots with meristems arose. The shoots were transferred to rooting medium (MSO plus kanamycin (26 ug/ml) and cefotaxime (50 ug/ml)). The shoots were cultured in growth boxes until they were of sufficient size for transfer to the green house.

Extraction of Tomato PME

PME was purified according to the following procedure. All operations were performed at 4° C. 600 g of tomatoes were homogenized in a Warring blender for 2 min in 1200 ml buffer (100 mM Na-succinate pH 6.2). 36 g solid NaCl was added to the homogenate to reach an end-concentration of 3% (w/v) in order to isolate membrane bound proteins. After 2 hours incubation with gently stirring at 4° C. the suspension was filtered through nylon mesh and the filtrate was centrifuged at 10,000 rpm for 20 min to remove insoluble residues.

The supernatant was then fractionated using $(NH_4)_2SO_4$ precipitation. The supernatant was first precipitated with 30% $(NH_4)_2SO_4$ under slowly stirring for 30 min. After centrifugation at 20,000 rpm for 10 min the supernatant was further precipitated with 60% $(NH_4)_2SO_4$ for 30 min. The suspension was centrifuged as before and the precipitate was resuspended in 50 ml 50 mM MES, 1 mM DTT pH 6.8 and dialysed against the same buffer over night.

Chromatography

The dialysed sample was further separated by cation exchange chromatography. A 40–50 ml sample was applied to a CM-Sepharose™ CL-6B (1.5×15 cm) in two rounds with a 30 min wash between the rounds with buffer A: 50 mM MES, 1 mM DTT pH 6.8. After washing off the unbound proteins with buffer A the bound proteins were eluted with an increasing NaCl gradient from 0–0.4 M NaCl in total 500 ml. The flow was 25 ml/h and fractions of 8.33 ml were collected. The protein absorption profile was measured at 280 nm. All fractions were analysed for PME activity and protein. The protein content was measured spectrophotometrically with the BioRad method.

Measurement of PME Activity

The PME activity of a crude/pure extract prepared from a transformed plant of the present invention can be determined quite readily. In this respect, PME catalyses the cleavage of methylester groups from pectin. During the purification steps PME can be detected by a fast method using methyl red indicator test. Due to cleavage of methyl groups from galacturonic acid residues in the pectin chain, carboxyl groups are formed and the pH will then drop in the assay. The pH indicator—methyl red—changes colour at pH drop from yellow (pH 6.2) to pink (pH 4.2). Typically, the assay will contain 1 ml 0.5% Grindsted™ Pectin 1450 (DE 70%) (supplied by Danisco Ingredients, Danisco A/S) solubilized in 0.15 M NaCl pH 7 and 25 µl sample. The samples which then show positive methyl red test after 10 min incubation at 30° C. are then further measured by the titration method (Versteeg et al (1978) Lebensmittel.-Wiss. u. Technol., 11: 267–274).

With the titration method the assay will typically contain 10 ml 0.5% lime pectin (Grindsted™ Pectin 1450—supplied by Danisco Ingredients, Danisco A/S) solubilized in 0.15 M NaCl pH 6.8 and 10–100 µl sample. Titration is performed with 0.02 M NaOH and the reaction is measured at room temperature. An automatic titrator can be used (Versteeg et al. (1978) Lebensmittel.-Wiss. u. Technol., 11: 267–274).

Characterisation of PME Activity

The purity of the PME fraction may be investigated by SDS-PAGE using Pharmacia PhastSystem™ with 10–15% SDS-gradient gels. Electrophoresis and silver staining of the proteins may be carried out as described by the manuals from Pharmacia. For determination of pI IEF 3-9 PhastSystem™ gels can be used.

Peptide Mapping

Further studies that can be performed on the PME include peptide mapping. In this respect, PME can be digested with either trypsin or endo-proteinase Lys-C from Lysobacter enzymogenes (both enzyme preparations should are sequencing grade)—which can be purchased from Boerhinger Mannheim, Germany.

Typically, 100 mg purified PME is carboxy methylated with iodoacetamide to protect the reduced SH-groups. Then the protein is cleaved with trypsin (4 mg/20–100 ml). The hydrolytic cleavage is performed at 40° C. for 2×3 hrs. The reaction is stopped with addition of 20 ml TFA. After centrifugation at 15,000 rpm for 5 min the peptides are purified on a reverse-phase HPLC column (Vydac 10 C18 column). 2×500 ml samples are applied. The peptides are eluted and separated with an increasing acetonitrile gradient from 0.05–0.35% in 60 min 0.1% TFA. The peptides are collected manually in Eppendorf tubes.

For digestion with endo-proteinase Lys-C, freeze dried PME (0.1 mg) is dissolved in 50 ml of 8 M urea, 0.4 M $NH_4CO_3$, pH 8.4. After overlay with $N_2$ and addition of 5 ml of 45 mM DTT, the protein is denatured and reduced for 15 min at 50° C. under $N_2$. After cooling to room temperature. 5 ml of 100 mM iodoacetamide is added for the cysteines to be derivatised for 15 min at room temperature in the dark under $N_2$. Subsequently, 90 ml of water and 5 mg of endo-proteinase Lys-C in 50 ml 50 mM tricine and 10 mM EDTA, pH 8.0, are added and the digestion was carried out for 24 hrs at 37° C. under $N_2$.

The resulting peptides are then separated as described for trypsin digested peptides.

Selected peptides can be further purified on a Devosil 3 $C_{18}$ RP-HPLC column 0.46×10 cm (Novo Nordisk, Denmark). The purified peptides are then applied on an amino acid sequencer, Applied Biosystems 476A, using pulsed-liquid fast cycles.

Generation of Antibodies to the PME Enzyme (for Measuring Total PME Protein and for Western Blotting Etc)

Antibodies can be raised against the enzyme of the present invention by injecting rabbits with the purified enzyme and isolating the immunoglobulins from antiserum according to procedures described according to N Harboe and A Ingild ("Immunization, Isolation of Immunoglobulins, Estimation of Antibody Titre" In A Manual of Quantitative Immunoelectrophoresis, Methods and Applications, N H Axelsen, et al (eds.), Universitetsforlaget, Oslo, 1973) and by T G Cooper ("The Tools of Biochemistry", John Wiley & Sons, New York, 1977).

Characterisation of Antibodies to PME

Immuno gel electrophoresis can be used for characterisation of antibodies (see later section)—such as polyclonal antibodies—raised against PME. The enzyme fractions are then separated on SDS-PAGE and transferred to NC-paper by semi-dry blotting technique on a Semidry transfer unit of the PhastSystem™. The NC-paper is incubated with the primer antibody diluted 1:50 and stained with the second antibody coupled to alkaline phosphatase (Dako A/S Glsotrup, Denmark) used in a dilution of 1:1000.

Measurement of PG Activity

PG activity was measured using polygalacturonan as substrate. The degradation of polygalacturonan by PG was followed by determination of an increase in reducing end groups with the method developed Somogyi and Nelson (Sturgeon (1990) In Methods in plant biochemistry (Eds.: P M Dey and J B Harborne), Academic Press, Harcourt Brace Jonanovich. Publishers, pp 1–37). 900 µl of 0.1% polygalacturonan solubilised in 50 mM Na-acetic acid pH 4.5 was incubated with 100 µl enzyme fraction at 40° C. Aliqouts of 125 µl were withdrawn after 0, 15 and 30 min incubation. The amount of reducing group in the 125 µl was determined as described by Sturgeon (1990).

Results I

Characterization of Transformed Plants and Fruit

Transformed tomato plants were recovered containing both the sense and antisense constructs. Both orientations of the nucleotide sequence resulted in transformed tomato lines with lowered levels of PG activity relative to PME activity even though total PME levels were unaltered. The best results were obtained in two transgenic lines carrying the antisense construct where levels of PG were so low as to be at the limit of detectability. In these two lines, recoverable PG activity represented less than 10% of the total PG activity in the fruit.

To test PME and PG enzyme levels, the fruit of transformed and control plants was classified as mature green 42 days after pollination and the breaker stage (about 45 days after pollination) was considered to be when the first visible external coloration of the fruit appeared. At least three fruit were collected from each plant seven days after breaker stage and the combined pericarp tissue for the fruit for each plant were analyzed. Cell wall proteins isolated from the plants were probed immunologically for levels of total PG protein and for PG and PME activity. Immunoblot analysis by SDS-PAGE separation and probing with respective antibodies revealed that the antisense plants of 4 lines had less than 10% PG as a proportion of total PG activity while the non-transformed control exhibited about 25% PG. PG levels in control and experimental lines remained similiar, at the sensitivity of a blot analysis. Further analysis confirmed that a reduction in extractable PG activity in 12 of 17 independently derived transformed antisense lines was due to a concomitant reduction in detectable PG protein level.

Detailed analysis was conducted on the one antisense line. Two copies of the inserted sequence were found and, by analysis of selfed progeny, it was determined that the two sequences segregated by Mendelian inheritance as a single locus. Fruit from plants were gathered at 24, 33, 37 and 42 days after pollination (dap). Western immunoblot analysis was conducted for presence of PG and PME. PME was first detectable in controls at 24 dap and accumulated throughout development and remained at high levels during ripening. PG in the fruit was almost undetectable at all stages of development.

RNA was extracted from the same fruit tissue samples from which protein samples had been taken. The analysis of RNA levels revealed that PME RNA in controls was detectable at 24 dap, reached maximum at 37 dap. In contrast, PG RNA was almost undetectable throughout fruit development and ripening.

Measurements of tomato serum viscosity verified the presence of viscosity increase that would be expected in tomato fruit extract from the presence of the higher levels of pectins.

Methods II

Effect of Tomato PME Treated Pectin on the Viscosity and Stability of Protein Drinks Enzymatic Treatment of Pectin with PME Derivable from Tomato A batch of enzymatically treated pectin was prepared as follows:

125 g pectin was dissolved in hot water under efficient stirring. 45.3 g NaCl (reagent grade) was added and the volume adjusted to 4.01 with water. This solution was stirred until the salt had dissolved. The pectin solution was cooled to 40° C. and the pH was increased to pH 7.0, using 1 N NaOH (reagent grade) and efficient stirring. An appropriate sample of tomato PME was added and the enzymatic reaction continued until the desired degree of estrification was achieved. The pH was kept constant at pH 7 by automatic dosage of 1 N NaOH (reagent grade) during the incubation period, and the enzymatic reaction was followed by the consumption of NaOH.

When the pectin sample had reached the desired degree of de-esterification the NaOH addition was stopped, the pH of the solution lowered to about 3.0 by addition of 2% HCl. The pectin solution was then heated to 70° C. for 5 min to completely inactivate the enzyme. The treated pectin was precipitated with 1 volume of isopropanol, washed with 60% isopropanol and pressed to about 50% dry matter. The enzymated pectin batch was then air dried at 40° C. and finally milled to a dry powder.

Determination of Pectin Samples for Calcium Sensitivity Index (CF)

Calcium sensitivity is measured as the viscosity of a pectin dissolved in a solution with 57.6 mg calcium/g pectin divided by the viscosity of exactly the same amount of pectin in solution, but without added calcium. A non calcium sensitive pectin has a CF value of 1.

4.2 g pectin sample is dissolved in 550 ml hot water with efficient stirring. The solution is cooled to about 20° C. and the pH adjusted to 1.5 with 1N HCl. The pectin solution is adjusted to 700 ml with water and stirred. 145 g of this solution is measured individually into 4 viscosity glasses. 10 ml water is added to two of the glasses (double determinations) and 10 ml of a 250 mM $CaCl_2$ solution is added to the other two glasses under stirring.

50 ml of an acetate buffer (0.5 M, pH about 4.6) is added to all four viscosity glasses under efficient magnetic stirring, thereby bringing the pH of the pectin solution up over pH 4.0. The magnets are removed and the glasses left overnight at 20° C. The viscosities are measured the next day with a Brookfield viscometer. The calcium sensitivity index is calculated as follows:

$$CF = \frac{\text{Viscosity of a solution with 57.6 mg Ca}^{2+}/\text{g pectin}}{\text{Viscosity of a solution with 0.0 mg Ca}^{2+}/\text{g pectin}}$$

Determination of Pectin Samples Degree of Esterification (% DE)

To 50 ml of a 60% isopropanol and a 5% HCl solution is added 2.5 g pectin sample and stirred for 10 min. The pectin solution is filtered through a glass filter and washed with 15 ml 60% isopropanol/5 % HCl solution 6 times followed by further washes with 60% isopropanol until the filtrate is free of chlorides. The filtrate is dried overnight at 80° C.

20.0 ml 0.5 N NaOH and 20.0 ml 0.5 N HCl is combined in a conical flask and 2 drops of phenolphtalein is added. This is titrated with 0.1 N NaOH until a permanent colour change is obtained. The 0.5 N HCl should be slightly stronger than the 0.5N NaOH. The added volume of 0.1 N NaOH is noted as $V_0$.

0.5 g of the dried pectin sample (the filtrate) is measured into a conical flask and the sample is moistened with 96% ethanol. 100 ml of recently boiled and cooled destined water is added and the resulting solution stirred until the pectin is completely dissolved. Then 5 drops of phenolphtalein are added and the solution titrated with 0.1 N NaOH (until a change in colour and pH is 8.5). The amount of 0.1 N NaOH used here is noted as $V_1$. 20.0 ml of 0.5 N NaOH is added and the flask shaken vigorously, and then allowed to stand for 15 min. 20.0 ml of 0.5 N HCl is added and the flask is shaken until the pink colour disappears. 3 drops of phenolphtalein are then added and then the resultant solution is titrated with 0.1 N NaOH. The volume 0.1 N NaOH used is noted as $V_2$.

The degree of esterification (% DE: % of total carboxy groups) is calculated as follows:

$$\% \ DE = \frac{V_2 - V_0}{V_1 + (V_2 - V_0)}$$

Acidified Milk Beverage Production

Standardised skimmed milk (17% MSNF), prepared from mixing powdered milk with adequate volume of de-ionised water at 68° C. for 20 minutes and cooled down to 30° C., was acidified at 30° C. with 3.3% glucone-delta-lactone (GDL) to about pH 4. The pectin sample was added as a sugar solution and stirred for 30 min. The acidified milk drink was homogenized at 200 bar at room temperature and then filled into sterile 250 ml plastic bottles. It was then heated on a water bath at 75° C. for 10 min with intervals of shaking for 5 minutes. Finally, the drink was cooled to room temperature and then stored overnight at 5° C.

Yoghurt Production

Standardised skimmed milk (prepared by mixing powdered milk with an adequate volume of water) was heated at 90° C. in 5 min and then homogenized at 200 kp/cm² and the milk cooled to 31° C. Yoghurt culture was added and the milk fermented to about pH 4.0. The yoghurt was cooled to about 20° C. and the pectin sample was added as a saturated sugar solution (about 65% sugar) and stirred for 15 min. The pH was adjusted to pH 4.0 with lactic acid. The yoghurt was pasteurized at 88° C. for 15 seconds and homogenized at 150 kp/cm², then cooled to 20° C. and filled into sterile 250 ml blue cap bottles (200 ml/bottle).

The composition of the final product was: 7.6% MSNF (milk solid content), 9.15% sugar and 0.25% or 0.35% pectin sample giving total solids of 17.0% or 17.10%, respectively.

Viscosity Determination of Yoghurt Drink

The viscosity of a yoghurt sample was determined (double determinations) using either a Bohlin Rheometer™ (supplied by Bohlin Instruments) with shear rates 18.5–46.0 or a using a Stress Tech™ (Rheologica instruments AB) with the same shear rates.

Protein Stability Measured by a Centrifugation Test 40 g of a sample (e.g. drinking yoghurt) is centrifuged at room temperature, 2800×g for 20 min. The supernatant is discarded and the centrifuge glass placed upside down for 5 min. The glass is weighed and the % sedimentation was calculated as follows:

$$\% \text{ Sedimentation} = \frac{\text{Wgt of glass after centri} - \text{Wgt of glass}}{\text{Wgt of sample}} \times 100$$

Where

Wgt = weight and centri = centrifugation

Protein Stability as Judged by Particle Size Distribution in the Sample

Particle size distribution of a yoghurt sample was determined by the use of a Malvern 2600 Easy™ sizer. The particle size is determined by laser light scattering by this method. 1 ml yoghurt sample was added to 9 ml de-areated buffer solution (30.7% 0.1 M citric acid. 19.3% 0.2 M $Na_2HPO_4$ and 50.0% water) and mixed. The de-areated buffer is added to the measuring glass and the mixture of sample/buffer is added droplet by droplet until the optimum concentration is obtained. The average particle size is calculated from the measurements.

A yoghurt with the average particle size below about 3 μm is considered rather stable while a yoghurt with an average particle size over about 10 μm and higher is considered not to be stable for long term storage.

Determination of Long-Term Stability

Samples were stored at 4° C. or at ambient temperature and the whey separation was measured (in mm of whey at the top of the sample, in the bottle). The sample was filled in 250 ml blue cap bottles (double determinations). The depth of the sample in each case was approximately 70 mm—which corresponded to the 200 ml mark for each bottle.

Results II

EXAMPLE 1

Sour Milk Drink

The purpose of adding pectin to a sour milk drink (e.g. a yoghurt drink) is to produce a drink that remains physically homogenous during the bacteriological and organoleptic shelf life of the drink. In addition the treatment of the yoghurt drink for long term storage destabilizes the protein in the drink giving rise to a drink with a sandy mouthfeel and showing rather quickly syneresis, if pectin is not added.

Treatment of the Pectin

A commercially available high ester pectin; Grindsted™ Pectin URS (Ultra Rapid Set pectin type) was chosen as the mother pectin, due to its high ester level (% DE of 82). The treatment with the tomato PME enzyme of this mother pectin is explained in the methods section.

The enzymatic reaction was stopped and the resulting experimental pectin (called Pectin T was investigated for its degree of esterification, by the method described in the method section. In addition, to compare the two pectin types, the mother pectin and the treated pectin, with a known good commercial drinking yoghurt pectin type, the Grindsted™ Pectin AM453 was included in the experiments.

The relative calcium sensitivity of the three chosen pectins was determined as explained in the method section: Determination of pectin samples calcium sensitivity index (CF), and the results are shown in the Table below.

| Pectin-type | CF | DE % |
|---|---|---|
| Grindsted ™ Pectin URS | 1.1 | 82 |
| Pectin T | 1.4 | 76 |
| Grindsted ™ Pectin AM453 | >20 | 72 |

De-esterification of the Grindsted™ Pectin URS mother pectin from 82% DE down to 76% DE gave nearly no change in the calcium sensitivity of the these two pectins (average CF of 1 have no sensitivity). A pectin with measurable calcium sensitivity could be produced by further treatment with the tomato PME enzyme on the mother pectin down to 70% DE, since this pectin had average CF of 14.

Results of Yoghurt/Drinking Yoghurt Analysis

Yoghurt was produced as explained in the method section. The three pectins (Grindsted™ Pectin URS, Pectin T and Grindsted™ Pectin AM453) were used individually in the following recipes:

7.6% MSNF (milk solid content), 9.15% sugar and 0.25% or 0.35% pectin sample giving total solids of 17.0% or 17.10%, respectively in the final product.

The quality of the individual yoghurt produced was investigated by their sedimentation % seen in the centrifugation test, by measuring the particle size in the yoghurt, by measuring the viscosity and by examination of possible whey separation during long time storage, as described in the method section.

The sedimentation of the yoghurt produced with the three pectin types are presented in the Table below.

| Pectin-type | SEDIMENT (IN %) OF THE YOGHURT | |
|---|---|---|
| | Concentration - 0.25% | Concentration - 0.35% |
| Grindsted ™ Pectin URS | 29.40 | 21.02 |
| Pectin T | 1.53 | 2.95 |
| Grindsted ™ Pectin AM453 | 2.20 | 1.85 |

The results are the average of from one to four individual production.

It is clear that the mother pectin (URS type) had a high sedimentation % and consequently the yoghurt produced showed whey separation and was unstable at both pectin concentrations used (0.25 and 0.35%). This is not surprising since normally the URS pectin type cannot be used for stabilization of heat treated yoghurt types for long time storage.

The yoghurt produced with the Pectin T showed stability at both pectin dosages used and low sedimentation as seen by the above results, and no whey separation after over 75 days of storage. In comparison, the excellent Grindsted™ Pectin AM453 normally used in yoghurt production also showed low sedimentation, as expected, and produced stable yoghurts with no whey separation (see results above).

By treating the mother URS pectin with tomato PME an unsuitable pectin was made suitable as a stabilizing agent in the yoghurt, and this treated pectin behave just as well as an excellent commercial stabilizer.

Futher examination of the produced yoghurts by particle size determination (see the methods section) were performed and the results are shown in the Table below.

PARTICLE SIZE (IN μM) OF THE YOGHURT

| Pectin-type | Concentration - 0.25% | Concentration - 0.35% |
| --- | --- | --- |
| Grindsted ™ Pectin URS | 9.32 | 6.41 |
| Pectin T | 1.33 | 1.55 |
| Grindsted ™ Pectin AM453 | 1.40 | 1.53 |

The average particle size (the number corresponding to the D(4.3)) fraction using the Malvern instrument, is shown) of the yoghurt produced with the mother URS pectin is high, as expected. Again the results are an average of one to four productions.

The average particle size of the yoghurt produced from both the Pectin T and the Grindsted™ Pectin AM453 are small at both pectin dosages used (see results above). Again showing that the yoghurt produced with these pectin types are suitable to produce stable yoghurts.

Finally, and very importantly, in the case of drinking yoghurt production for long time storage, the viscosity was determined and the results are shown in the Table below.

VISCOSITY (IN MPa s) OF THE YOGHURT

| Concentration/ Pectin-type | Concentration - 0.25% | Concentration - 0.35% |
| --- | --- | --- |
| Grindsted ™ Pectin URS | 55 | 40 |
| Pectin T | 12 | 18 |
| Grindsted ™ Pectin AM453 | 24 | 43 |

Since the mother URS pectin could not stabilize the yoghurt the viscosity obtained is, as expected rather high at both pectin concentrations. The excellent Grindsted™ Pectin AM453 which produced stable yoghurts with low sedimentation and low particle size showed a viscosity of about half the viscosity seen with the Grindted™ Pectin URS pectin at the 0.25% pectin dosage and approximately the same as the URS pectin at the 0.35% pectin dosage—irrespective of the fact that only the AM453 pectin produced a stable yoghurt.

In both the URS and the AM453 cases the higher viscosity seen could partly be attributed to the amount of pectin added, especially this seems to be the situation in the AM453 pectin case since an increase in the amount of pectin added (from 0.25 to 0.35%) produced nearly twice as viscous a yoghurt.

The viscosity obtained with the tomato treated PME Pectin T shows a dramatic fall in viscosity compared with the mother URS pectin at 0.25% concentration. This is partly due to the stabilization of the yoghurt with the Pectin T but not the only reason since the AM453 yoghurt has twice as high a viscosity at that pectin dosage. Indeed, adding 0.35% of the Pectin T to the yoghurt only increases the viscosity with 6 units (compared with the 0.25% dosage) while the viscosity increases with 19 units going from 0.25% to 0.35% in the AM453 case.

The tomato PME treated Pectin T can stabilize yoghurt having a very low viscosity, despite the pectin dosage was 0.25% (or 0.35%), which gave nealy twice as high a viscosity using other untreated pectins—e.g. Grindsted™ Pectin AM453.

This is a new and very important development for the production of sour milk drinks.

By treating the Grindsted™ Pectin URS with tomato PME a new pectin type is created which in contrast to the mother pectin can stabilize yoghurt and most importantly shows much lower viscosity than normally used pectins. Other high ester pectin can also be improved by treatment with the tomato PME.

EXAMPLE 2

Whey Juice Drink

The modified pectin according to the present invention (as prepared above) was used in a whey juice drink as follows:

Sweet or acid whey 42.00%
Fruit juice 40.00%
Sugar 8.00%
Sodium citrate 0.20%
PME modified pectin 0.20%
Grindsted Flovouring +
Water 9.60%

Dry PME modified pectin, sodium citrate and sugar were mixed and then dissolved in water at 80° C. This pectin solution was cooled to below 5° C. and whey was added at 5° C. Grindsted Flavouring (supplied by Danisco Ingredients, Danisco A/S) and juice were added slowly and the pH in the sample mixture was adjusted with citric or lactic acid to pH 4.0. The sample mixture was aged for approx. 30 min under agitation. The pasteurisation was performed at 80° C./15 seconds and homogenisation at 200 bar (2900 psi). The samples were cooled to 20° C. and filled aseptically in containers.

Sample tests were analysed after 24 hours, 1 months and 6 months incubation at room temperature. The investigation analysis included viscosity measurements, stability index particle size and long-term stability—the protocols for which are described above.

The results showed improved stability and a long-term stability in the whey juice drink processed with PME modified pectin compared to the reference pectin employed in the control tests. In addition, the whey juice drink had a favourable viscosity which was lower than the control drinks.

The whey juice drink was also processed with plant PME modified lime and lemon pectin, respectively,—i.e. modified with the PME of the present invention. The results demonstrate that PME modified pectin has improved protein stability compared to the non-modified pectin and also compared to the reference pectin.

EXAMPLE 3

Milk/Fruit Juice Drink

Grindsted™ URS (obtained from Danisco Ingredients, Danisco A/S) was modified with the PME as described for the yoghurt drink. The modified pectin was used in a milk/fruit juice drink which contained:
Skimmed milk 45.00%
Fruit juice 40.00%
Sugar 5.00%
PME modified pectin 0.25%
Grindsted Flovouring +
Water 9.75%

Dry PME modified pectin and sugar were mixed and then dissolved in water at 80° C. The pectin solution was cooled to below 5° C. and milk was added at 5° C. Grindsted Flavouring and juice were added slowly and the pH in the sample mixture was adjusted (if necessary) with citric or lactic acid to pH 4.0. The sample mixture was aged, pasteurised and homogenised as described for whey juice drink. The samples were cooled to 20° C. and filled aseptically in containers.

The results showed improved stability—including long-term stability—in the milk/fruit juice drink processed with PME modified pectin compared to the reference pectin employed in the control tests. In addition, the milk/fruit juice drink had a favourable viscosity which was lower than the control drinks. Improved functionality was also observed.

The milk/fruit juice drink can also be processed with lime and lemon pectin modified with the PME of the present invention.

EXAMPLE 4

Whey Stability

The enzymatic modified pectins were tested at pH 4.0. The pH of the resultant pectin solutions were adjusted to pH 4.0 with KOH/HCl. The pectin concentration was adjusted to 1.0%. The pectins were tested in concentrations of 0.1%–0.25%. Pectin. Jenness Buffer (see below) and whey solution (see below) were mixed and heated at 96° C. for 25 min. After cooling to room temperature the absorbance is measured at 500 nm.

Dry Blend Jenness Buffer:

Dry Powder Jenness (described in Jenness, R and Koops, J *Preparation and Properties of a salt solution which simulates milk ultrafiltrate*, Nederlands Melk-en Zuiveltijd-schrift, vol 16 nr 3, pp 153–164, 1962):
15.80 g $KH_2PO_4$
5.08 g $K_3$ citrate
17.91 g $Na_3$ citrate, $2.H_2O$
1.80 g g $K_2SO_4$
13.20 g $CaCl_2$, $2.H_2O$
5.02 g $Mg_3$ citrate, $H_2O$
3.00 g $K_2CO_3$
10.78 g KCl Buffer Solution:

Aqueous solution of 7.5900 g/l Dry Powder Jenness with a pH of 4.0.

Whey Solution

A concentrate of whey protein is freeze dried and pulverized. A solution of 0.40% w/w whey protein is prepared in Jenness Buffer at pH 4.0.

Pectin Solutions

1% w/w aqueous solutions of pectins are made with a pH of 4.0.

Mixture Concentrations:

Pectin, Jenness Buffer and Whey solution are mixed as indicated in the Table below. The mixtures are heated at 96° C. for 25 minutes and after cooling to room temperature the samples are measured on a spectrophotometer at 500 nm.

| μl pectin solution | μl Jenness Buffer | μl whey solution | μl total volume |
|---|---|---|---|
| 500 | 2000 | 2500 | 5000 |
| 750 | 1750 | 2500 | 5000 |
| 1000 | 1500 | 2500 | 5000 |
| 1250 | 1250 | 2500 | 5000 |

Results

The results are shown in the Table below. The quoted absorbance value at 500 nm is a mean value taken from two measurements. For comparison between the different types of pectin and the enzymatic modified pectins according to the present invention the index for non-modified pectin Grindsted™ Pectin 3450 (supplied by Danisco Ingredients, Danisco A/S) is set to 100.

An Index of >100 indicates poorer protein stability than using the sample 3450. An Index of 100 indicates similar stability to the sample 3450. An Index of <100 indicates better protein stability than using the sample 3450. An Index of 95 or <95 indicates very good protein stability.

| Pectin type | 0.10% pectin | 0.15% pectin | 0.20% pectin | 0.25% pectin |
|---|---|---|---|---|
| Grindsted ™ pectin 3450 | 100 | 100 | 100 | 100 |
| Grindsted ™ pectin URS | 127 | 140 | 155 | 161 |
| 5 min enz. | 100 | 108 | 115 | 113 |
| 10 min enz. | 98 | 106 | 111 | 111 |
| 15 min enz. | 92 | 94 | 100 | 100 |
| 20 min enz. | 90 | 95 | 100 | 99 |

As can be seen from the results the Grindsted™ pectin URS pectin modified according to the present invention exhibits favourable properties and in some instances very good properties for increasing stability when compared to the reference Grindsted™ pectin 3450 and the unmodified Grindsted™ pectin URS pectin.

EXAMPLE 5

Laban Drink with Long Shelf Life, Low pH

The Laban drink is an acidified milk drink with a pH value below 4.2. The laban drink consists of Laban base mixed with pectin solution. The formulation for laban base is:

Anhydrous milk fat 2.8%
Skimmed milk powder 10.0%
Grindsted flavouring +
Water 87.2%

Standardised whole milk (anhydrous milk fat and skimmed milk powder) is homogenised at 75–80° C. and pressure of 200 bar (2900 psi) followed by pasteurisation at 90–95° C. for 5–10 min. After culturing to pH around 4.0 the pH is adjusted to 3.8–4.2 with citric or lactic acid. Pectin solution is then added. The mixture is then agitated until it is a homogeneous mixture. It is then pasteurised at 90–95° C. for 10–15 seconds and further homogenised at 150–200 bar. After cooling to 20–25° C. the product is filled aseptically in containers.

After a few days, non-stabilised laban drink often show syneresis.

However, addition of the enzymatically modified pectin according to the present invention prevents syneresis and improves the viscosity.

In addition, the product has a pronounced yoghurt taste and a long shelf life.

EXAMPLE 6

Orange Juice (Protein-Enriched)

Orange juice drink is an acidified drink (pH approx. 4) containing 2% DANPROLACT 40™ (Central Soya, Aarhus A/S), 6% sugar, 10% orange concentrate, 0.4% lemon concentrate, 0.2% pectin and 81.4% water. The product is an orange juice drink enriched with soya protein. The product is pasteurised and homogenised. After cooling to 20–25° C. the product is filled aseptically in containers and can be stored for approx. 6 months at room temperature. Addition of enzymatically modified pectins according to the present invention in orange drink (protein-enriched) showed favourable properties—such as long term stability—and it had a good mouth feel.

Discussion

The present invention demonstrates that a process for modifying a pectin using an antisense technique, provides transformed tomato plants with silenced PG activity in the sense that they have dramatically decreased levels of native PG enzyme, due to the inhibition of expression of the PG gene. These transformed plants have about a 95% or greater reduction in PG activity and an elevated PME to PG ratio which is used to modify the pectin of the present invention.

As is normally the case, the transformed tomato lines created were found to vary somewhat in the extent of PG suppression, but two transformed lines were created in which the total level of extractable PG activity was reduced to less than 10% of total PG activity of the wild type.

Treatment of high ester pectins (such as Grindsted™ Pectin URS) with the tomato PME of the present invention yielded a pectin which stabilized yoghurt and which showed much lower viscosity than normally used pectins.

Whey juice drink processed with the PME modified pectin of the present invention showed improved long-term stability when compared with control tests. In addition, the whey juice drink had a favourable viscosity which was lower than the control drinks.

Milk/fruit juice drink processed with the PME modified pectin of the present invention showed an improved stability—including long-term stability—compared with the control pectin. In addition, the milk/fruit juice drink had a favourable viscosity which was lower than the control drinks. An improved functionality was also observed.

Addition of a PME modified pectin of the present invention to a Laban drink prevented syneresis and improved the viscosity of the drink. In addition, the product had a pronounced yoghurt taste and a long shelf life.

SUMMARY

The native PG protein was purified from ripe tomato fruit and cDNA clones encoding the protein were isolated and sequenced. These cDNA clones were used in the production of a transformed line of tomato in which the expression of the PG enzyme was substantially silenced by an antisense construct.

The present invention demonstrates the surprising finding it is possible to silence PG activity by differentially regulating the relative level of expression of PME and PG so that (i) the ratio of PME to PG is increased and a PME modified pectin of relatively high molecular weight (50 kDa to 200 kDa) is obtained.

The PME modified pectin of the present invention imparted an increased functionality to food products such as yoghurt, milk/fruit juice and whey or soya comprising drinks in terms of an improved viscosity and a longer shelf-life.

Thus, in summary, the present invention provides a process for modifying pectin by silencing PG activity which also allows an alteration of the ratios of the pectin degrading enzymes which are present. In particular, the present invention provides a process for modifying a pectin comprising decreasing the in situ levels of PG which is advantageous in terms of increasing the relative levels of PME and hence elevating the in situ PME:PG ratio.

All modifications to the present invention will be apparent to those skilled in the art.

For example, it would be possible to have a process of modifying a pectin using a PME extract; wherein the PME extract is obtained from a host that has had PG activity silenced; wherein the host comprises PME activity; and wherein said PME activity can be natural PME activity, additional PME activity, new PME activity or inserted PME activity.

All publications mentioned in the above specification are herein incorporated by reference. By way of example, the teachings and sequence listings provided in Dang Wei et al (1994) 36: 171–177 are incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A process for producing a modified pectin comprising:
   (i) providing a plant host having Pectin Methyl Esterase (PME) activity and polygalacturonase (PG) activity;
   (ii) transforming said host by silencing PG activity thereby to provide an increased PME to PG ratio;
   (iii) preparing a PME extract from the transformed host;
   (iv) contacting the PME extract with a pectin to produce the modified pectin,
   said silencing comprising expression of SEQ ID No: 1 or SEQ ID NO:3 in an antisense orientation.

2. A process according to claim 1 wherein the process includes the further step of isolating the PME modified pectin from the active PME.

3. A process according to claim 1 wherein the PME modified pectin is a high ester pectin.

4. A process according to claim 2 wherein the PME modified pectin contains from about 55% to about 85% ester groups.

5. A process according to claim 1 wherein the process includes the further step of adding the modified pectin to a medium that is suitable for consumption.

6. A process according to claim 5 wherein the medium is an acidic environment.

7. A process according to claim 6, wherein the acidic environment has a pH of from about 3.5 to about 5.5.

8. A process according to claim 7, wherein the acidic environment has a pH of about 4.

9. A process according to claim 6 wherein the medium is a beverage.

10. A process according to claim 9 wherein the beverage is an acidified milk beverage, a drinking yoghurt, a fruit juice, milk beverage or a beverage comprising whey protein or a vegetable protein.

11. A process according to claim 9 wherein the medium comprises a protein.

12. A process for producing a modified pectin comprising:
   (i) providing a host plant cell having Pectin Methyl Esterase (PME) activity and polygalacturonase (PG) activity;
   (ii) transforming the host plant cell with a construct comprising a recombinant DNA sequence such that the ratio of PME to PG in said host plant cell is increased;
   (iii) preparing a PME extract from the transformed host plant cell; and
   (iv) contacting the PME extract with a pectin to produce the modified pectin,
   said transforming comprising expression of SEQ ID No: 1 or SEQ ID NO:3 in an antisense orientation.

13. The process of claim 12 wherein said PME extract is produced from a plant comprising said plant cell.

14. The process of claim 12 further comprising isolating said modified pectin from said PME extract to produce isolated modified pectin.

15. The process of claim 12 wherein said isolated modified pectin is high ester pectin.

16. The process of claim 14 wherein said isolated modified pectin contains from about 55% to about 85% ester groups.

17. The process of claim 12 further comprising adding the modified pectin to a medium that is suitable for consumption.

18. The process of claim 17 wherein the medium is an acidic environment.

19. The process of claim 18 wherein the medium is a beverage.

20. The process of claim 19 wherein the beverage is an acidified milk beverage, a drinking yoghurt, a fruit juice, a milk beverage, a beverage comprising whey protein, or a beverage comprising a vegetable protein.

* * * * *

SEQUENCE LISTING

<160> NUMBER OF SEQ ID NOS: 7

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Lys Ala Arg Lys Glu Ala Glu Leu Ala Ala Ala Thr Ala Glu Gln
 1               5                  10                  15

<210> SEQ ID NO 2
<211> LENGTH: 36
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Pro Cys His Leu Asn Cys Ser Leu Gln Thr Leu Ser Pro Thr Arg Thr
 1               5                  10                  15

Thr Pro Arg Lys His Cys Lys His Cys Phe Lys Thr Leu Ser Glu Lys
            20                  25                  30

Met Lys Trp Asn
        35

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Asn Glu Ala Tyr Val His Asp Gly Pro Val Arg Ser Leu Asn
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Gly Val Val Trp Phe Lys Asp Ser Val Gly Val Ser Gly Asn
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Lys Pro Ala Lys Ser Ala Arg Ser Val Arg Ser Gln Arg
 1               5                  10

-continued

```
<210> SEQ ID NO 6
<211> LENGTH: 27
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 6

Thr His Thr Thr Ser Gln Thr Thr Leu Arg Asp Pro Asp Val Tyr Ala
  1               5                  10                  15

Gly Ala Arg Trp Val Thr Trp Arg Val Gly Ala
             20                  25

<210> SEQ ID NO 7
<211> LENGTH: 8
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 7 ggccggcc                                                            8
```